(12) United States Patent
Mannino

(10) Patent No.: US 8,951,471 B2
(45) Date of Patent: Feb. 10, 2015

(54) JET ASSEMBLY FOR USE IN DETECTORS AND OTHER DEVICES

(75) Inventor: Rosario Mannino, North Haven, CT (US)

(73) Assignee: Perkinelmer Health Sciences, Inc., Waltham, MA (US)

( * ) Notice: Subject to any disclaimer, the term of this patent is extended or adjusted under 35 U.S.C. 154(b) by 271 days.

(21) Appl. No.: 13/035,938

(22) Filed: Feb. 26, 2011

(65) Prior Publication Data

US 2011/0211993 A1    Sep. 1, 2011

Related U.S. Application Data

(60) Provisional application No. 61/308,499, filed on Feb. 26, 2010.

(51) Int. Cl.
  *G01N 33/00* (2006.01)
  *G01N 30/68* (2006.01)
(52) U.S. Cl.
  CPC .......... *G01N 30/68* (2013.01); *G01N 2030/685* (2013.01)
  USPC ................................ 422/54; 422/89; 422/94
(58) Field of Classification Search
  CPC .......................... G01N 2030/685; G01N 30/68
  USPC ............................................ 422/54, 89, 94
  See application file for complete search history.

(56) References Cited

U.S. PATENT DOCUMENTS

| | | | |
|---|---|---|---|
| 4,999,162 A * | 3/1991 | Wells et al. .................... | 422/54 |
| 5,811,665 A | 9/1998 | Gregor | |
| 6,662,626 B2 | 12/2003 | Van Der Maas | |
| 6,666,074 B2 | 12/2003 | Gerner | |
| 6,907,796 B2 | 6/2005 | Bremer | |
| 7,384,457 B2 | 6/2008 | Emmons | |
| 2002/0185441 A1 | 12/2002 | Gjerde | |
| 2004/0236083 A1 | 11/2004 | Libert | |
| 2007/0181479 A1 | 8/2007 | Yamamoto | |
| 2007/0283746 A1 | 12/2007 | Gerhardt | |

FOREIGN PATENT DOCUMENTS

GB         10742416        6/1967

OTHER PUBLICATIONS

ISR/WO for PCT/US2011/026241 Dated Apr. 26, 2011.
ISR/WO for PCT/US2011/026385 Dated May 2, 2011.

\* cited by examiner

*Primary Examiner* — Sam P Siefke
(74) *Attorney, Agent, or Firm* — Rhodes IP PLC; Christopher R Rhodes

(57) ABSTRACT

Certain embodiments described herein are directed to jet assemblies that include a substantially inert fluid flow path. In some examples, a jet assembly includes a fluid flow path comprising a substantially inert metal in a fluid flow path. Devices and systems using the jet assembly are also described. In other embodiments, a brazeless or weldless jet assembly is provided. In some embodiments, the brazeless jet assembly may include an inert material or coating, e.g., a silica coating, in a fluid flow path.

21 Claims, 21 Drawing Sheets

JET ASSEMBLY FOR USE IN DETECTORS AND OTHER DEVICES

PRIORITY APPLICATION

This application claims priority to, and the benefit of, U.S. Provisional Application No. 61/308,499 filed on Feb. 26, 2010, the entire disclosure of which is hereby incorporated herein by reference for all purposes.

RELATED APPLICATION

This application is related to commonly owned provisional application No. 61/308,461 filed on Feb. 26, 2010, the entire disclosure of which is hereby incorporated herein by reference for all purposes.

TECHNOLOGICAL FIELD

Certain embodiments herein are directed to a jet assembly that includes a substantially inert fluid flow path. In particular, certain embodiments are directed to a flame photometric detector jet assembly that includes a substantially inert fluid flow path.

BACKGROUND

Many chromatography systems use detectors that burn a sample in a flame. In some instances, the sample can react with hot surfaces in the flame jet assembly, which can cause the analyte to render it difficult or impossible to detect certain analytes in the sample.

SUMMARY

In an aspect, a jet assembly for use in a flame detector, the jet assembly comprising a fluid flow path in a housing, in which the fluid flow path is constructed and arranged to be fluidically coupled to a chromatography column to receive sample from the chromatography column, and in which the fluid flow path comprises a substantially inert material is provided. In some examples, the fluid flow path comprises a substantially inert metal material. In other examples, the flame detector can be a flame photometric detector, a flame ionization detector, a nitrogen-phosphorous detector or other flame based detectors.

In certain embodiments, the substantially inert metal material is present in a major amount. In other embodiments, the substantially inert metal material comprises titanium, aluminum, yttrium or combinations thereof. In additional embodiments, the substantially inert metal material comprises titanium oxide, aluminum oxide, yttrium oxide or combinations thereof. In some embodiments, the substantially inert metal material comprises nickel. In other embodiments, the substantially inert metal material is a Hastelloy® alloy. In some embodiments, the substantially inert metal material comprises chromium. In certain embodiments, the substantially inert metal material is an Inconel® alloy. In additional embodiments, the substantially inert metal material is present in a non-coated form. In some embodiments, the substantially inert metal material is in a tube that is integral to the housing.

In another aspect, a jet assembly for use in a flame detector, the jet assembly comprising a fluid flow path in a housing, in which the fluid flow path is constructed and arranged to be fluidically coupled to a chromatography column to receive sample from the chromatography column, and in which the fluid flow path comprises a non-catalytic material present in an effective amount to deter catalysis in the fluid flow path is described. In certain examples, the fluid flow path comprises a non-catalytic metal material. In other examples, the flame detector can be a flame photometric detector, a flame ionization detector, a nitrogen-phosphorous detector or other flame based detectors.

In certain examples, the non-catalytic metal material is present in a major amount. In other examples, the non-catalytic metal material comprises titanium, aluminum, yttrium or combinations thereof. In additional examples, the non-catalytic metal material comprises titanium oxide, aluminum oxide, yttrium oxide or combinations thereof. In further examples, the non-catalytic metal material comprises nickel. In yet other examples, the non-catalytic metal material is a Hastelloy® alloy. In some examples, the non-catalytic metal material comprises chromium. In additional examples, the non-catalytic metal material is an Inconel® alloy. In further examples, the non-catalytic metal material is present in a non-coated form. In some examples, the non-catalytic metal material is in a tube that is integral to the housing.

In an additional aspect, a jet assembly comprising a first tube configured to couple to a flame detector assembly, and a second tube inside the first tube, in which the second tube comprises a fluid flow path that is constructed and arranged to be fluidically coupled to a chromatography column to receive sample from the chromatography column, and in which the fluid flow path comprises a non-catalytic material present in an effective amount to deter catalysis in the fluid flow path is disclosed. In certain examples, the fluid flow path comprises a non-catalytic metal material.

In certain embodiments, the non-catalytic metal material comprises titanium, aluminum, yttrium or combinations thereof. In other embodiments, the non-catalytic metal material comprises titanium oxide, aluminum oxide, yttrium oxide or combinations thereof. In additional embodiments, the non-catalytic metal material comprises nickel. In further embodiments, the non-catalytic metal material is a Hastelloy® alloy. In some embodiments, the non-catalytic metal material comprises chromium. In some examples, the non-catalytic metal material is an Inconel® alloy. In additional examples, the non-catalytic metal material is present in a non-coated form. In further examples, the second tube is longer than the first tube to fluidically couple to the chromatography column. In other examples, the first tube comprises a non-catalytic material.

In another aspect, a jet assembly comprising a first tube configured to couple to a flame detector assembly, and a second tube inside the first tube, in which the second tube comprises a fluid flow path that is constructed and arranged to be fluidically coupled to a chromatography column to receive sample from the chromatography column, and in which the fluid flow path comprises a major amount of a substantially inert material is provided. In certain embodiments, the substantially inert material is a substantially inert metal material.

In some examples, the substantially inert metal material comprises titanium, aluminum, yttrium or combinations thereof. In other examples, the substantially inert metal material comprises titanium oxide, aluminum oxide, yttrium oxide or combinations thereof. In additional examples, the substantially inert metal material comprises nickel. In certain examples, the substantially inert metal material is a Hastelloy® alloy. In further examples, the substantially inert metal material comprises chromium. In other examples, the substantially inert metal material is an Inconel® alloy. In some examples, the substantially inert metal material is present in a non-coated form. In additional examples, the second tube is longer than the first tube to fluidically couple to the chromatography column. In further examples, the first tube comprises a substantially inert metal material.

In an additional aspect, a jet assembly comprising a fluid flow path inside a housing, in which the fluid flow path comprises a non-catalytic, non-glass material present in an effective amount to deter catalysis is described.

In some embodiments, the non-catalytic, non-glass material comprises titanium, aluminum, yttrium or combinations thereof. In other embodiments, the non-catalytic, non-glass material comprises titanium oxide, aluminum oxide, yttrium oxide or combinations thereof. In additional embodiments, the non-catalytic, non-glass material comprises nickel. In further embodiments, the non-catalytic, non-glass material is a Hastelloy® alloy. In some embodiments, the non-catalytic, non-glass material comprises chromium. In other embodiments, the non-catalytic, non-glass material is an Inconel® alloy. In additional embodiments, the non-catalytic, non-glass material is present in a non-coated form. In some embodiments, the non-catalytic, non-glass material is in a tube that is integral to the housing. In other embodiments, the housing is configured as a first tube.

In another aspect, a jet assembly comprising a fluid flow path inside a housing, in which the fluid flow path comprises, in which the fluid flow path comprises a substantially inert non-glass, non-stainless steel material is disclosed.

In certain examples, the substantially inert non-glass, non-stainless steel material comprises titanium, aluminum, yttrium or combinations thereof. In other examples, the substantially inert non-glass, non-stainless steel material comprises titanium oxide, aluminum oxide, yttrium oxide or combinations thereof. In additional examples, the substantially inert non-glass, non-stainless steel material comprises nickel. In further examples, the substantially inert non-glass, non-stainless steel material is a Hastelloy® alloy. In some examples, the substantially inert non-glass, non-stainless steel material comprises chromium. In other examples, the substantially inert non-glass, non-stainless steel material is an Inconel® alloy. In additional examples, the substantially inert non-glass, non-stainless steel material is present in a non-coated form. In certain examples, the substantially inert non-glass, non-stainless steel material is in a tube that is integral to the housing. In other examples, the housing is configured as a first tube.

In an additional aspect, a jet assembly insert that is constructed and arranged to couple to a housing of a jet assembly, the jet assembly insert comprising a fluid flow path that is configured to be fluidically coupled to a chromatography column, in which the fluid flow path comprises a substantially inert material is provided. In some examples, the substantially inert material is a substantially inert metal material.

In certain embodiments, the substantially inert metal material is present in a major amount. In other embodiments, the substantially inert metal material comprises titanium, aluminum, yttrium or combinations thereof. In additional embodiments, the substantially inert metal material comprises titanium oxide, aluminum oxide, yttrium oxide or combinations thereof. In further embodiments, the substantially inert metal material comprises nickel or chromium.

In another aspect, a jet assembly insert that is constructed and arranged to couple to a housing of a jet assembly, the jet assembly insert comprising a fluid flow path that is configured to be fluidically coupled to a chromatography column, in which the fluid flow path of comprises a non-catalytic material present in an effective amount to deter catalysis in the fluid flow path is provided. In some examples, the non-catalytic material is a non-catalytic metal material.

In certain examples, the non-catalytic metal material is present in a major amount. In other examples, the non-catalytic metal material comprises titanium, aluminum, yttrium or combinations thereof. In additional examples, the non-catalytic metal material comprises titanium oxide, aluminum oxide, yttrium oxide or combinations thereof. In other examples, the non-catalytic metal material comprises nickel or chromium.

In an additional aspect, a jet assembly insert that is constructed and arranged to couple to a housing of a jet assembly, the jet assembly insert comprising a fluid flow path that is configured to be fluidically coupled to a chromatography column, in which the fluid flow path comprises a non-catalytic metal oxide material present in an major amount to deter catalysis is described.

In certain embodiments, the non-catalytic metal oxide material is present in a major amount. In other embodiments, the non-catalytic metal oxide material comprises titanium, aluminum, yttrium or combinations thereof. In some embodiments, the non-catalytic metal oxide material comprises titanium oxide, aluminum oxide, yttrium oxide or combinations thereof. In additional embodiments, the non-catalytic metal oxide material comprises nickel or chromium.

In another aspect, a jet assembly insert that is constructed and arranged to couple to a housing of a jet assembly, the jet assembly insert comprising a fluid flow path that is configured to be fluidically coupled to a chromatography column, in which the fluid flow path comprises a substantially inert metal oxide material is disclosed.

In certain examples, the substantially inert metal oxide material is present in a major amount. In other examples, the substantially inert metal oxide material comprises titanium, aluminum, yttrium or combinations thereof. In additional examples, the substantially inert metal oxide material comprises titanium oxide, aluminum oxide, yttrium oxide or combinations thereof. In further examples, the substantially inert metal oxide material comprises nickel or chromium.

In an additional aspect, a flame detector comprising a flame jet, and a fluid flow path that is constructed and arranged to be fluidically coupled to a chromatography column at one end and to the flame jet at an opposite end, the fluid flow path comprising a substantially inert material, e.g., a substantially inert metal material, is provided. In some examples, the flame detector can be a flame photometric detector, a flame ionization detector, a nitrogen-phosphorous detector or other flame based detectors.

In certain embodiments, the substantially inert metal material is present in a major amount. In other embodiments, the substantially inert metal material comprises titanium, aluminum, yttrium or combinations thereof. In some embodiments, the substantially inert metal material comprises titanium oxide, aluminum oxide, yttrium oxide or combinations thereof. In additional embodiments, the substantially inert metal material comprises nickel or chromium.

In another aspect, a flame detector comprising a flame jet, and a fluid flow path that is constructed and arranged to be fluidically coupled to a chromatography column at one end and to the flame jet at an opposite end, the fluid flow path comprising a non-catalytic material, e.g., a non-catalytic metal material, present in an effective amount to deter catalysis in the fluid flow path is described. In some embodiments, the flame detector can be a flame photometric detector, a flame ionization detector, a nitrogen-phosphorous detector or other flame based detectors.

In certain examples, the non-catalytic metal material is present in a major amount. In other examples, the non-catalytic metal material comprises titanium, aluminum, yttrium or combinations thereof. In additional examples, the non-catalytic metal material comprises titanium oxide, aluminum oxide, yttrium oxide or combinations thereof. In some examples, the non-catalytic metal material comprises nickel or chromium.

In an additional aspect, a flame detector comprising a flame jet, and a fluid flow path that is constructed and arranged to be fluidically coupled to a chromatography column at one end and to the flame jet at an opposite end, the fluid flow path comprising a substantially inert metal oxide material is disclosed. In certain embodiments, the flame detector can be a flame photometric detector, a flame ionization detector, a nitrogen-phosphorous detector or other flame based detectors.

In some examples, the substantially inert metal oxide material is present in a major amount. In additional examples, the substantially inert metal oxide material comprises titanium, aluminum, yttrium or combinations thereof. In other examples, the substantially inert metal oxide material comprises titanium oxide, aluminum oxide, yttrium oxide or combinations thereof. In further examples, the substantially inert metal oxide material comprises nickel or chromium.

In another aspect, a flame detector comprising a flame jet, and a fluid flow path that is constructed and arranged to be fluidically coupled to a chromatography column at one end and to the flame jet at an opposite end, the fluid flow path comprising a non-catalytic metal oxide material present in an major amount to deter catalysis is described. In certain examples, the flame detector can be a flame photometric detector, a flame ionization detector, a nitrogen-phosphorous detector or other flame based detectors.

In certain embodiments, the non-catalytic metal oxide material is present in a major amount. In other embodiments, the non-catalytic metal oxide material comprises titanium, aluminum, yttrium or combinations thereof. In additional embodiments, the non-catalytic metal oxide material comprises titanium oxide, aluminum oxide, yttrium oxide or combinations thereof. In further embodiments, the non-catalytic metal oxide material comprises nickel or chromium.

In an additional aspect, a flame detector comprising a flame jet, and a fluid flow path that is constructed and arranged to be fluidically coupled to a chromatography column at one end and to the flame jet at an opposite end, the fluid flow path comprising a non-catalytic, non-glass material present in an effective amount to deter catalysis is provided. In some examples, the flame detector can be a flame photometric detector, a flame ionization detector, a nitrogen-phosphorous detector or other flame based detectors.

In certain examples, the non-catalytic, non-glass material is present in a major amount. In other examples, the non-catalytic, non-glass material comprises titanium, aluminum, yttrium or combinations thereof. In additional examples, the non-catalytic, non-glass material comprises titanium oxide, aluminum oxide, yttrium oxide or combinations thereof. In some examples, the non-catalytic, non-glass material comprises nickel or chromium.

In another aspect, a flame detector comprising a flame jet, and a fluid flow path that is constructed and arranged to be fluidically coupled to a chromatography column at one end and to the flame jet at an opposite end, the fluid flow path comprising a substantially inert non-glass, non-stainless steel material is disclosed. In certain examples, the flame detector can be a flame photometric detector, a flame ionization detector, a nitrogen-phosphorous detector or other flame based detectors.

In some embodiments, the substantially inert non-glass, non-stainless steel material is present in a major amount. In other embodiments, the substantially inert non-glass, non-stainless steel material comprises titanium, aluminum, yttrium or combinations thereof. In additional embodiments, the substantially inert non-glass, non-stainless steel material comprises titanium oxide, aluminum oxide, yttrium oxide or combinations thereof. In further embodiments, the substantially inert non-glass, non-stainless steel material comprises nickel or chromium.

In another aspect, a brazeless and weldless jet assembly for use in a flame detector is provided. In some embodiments, the jet assembly comprises a fluid flow path in a first tube, the fluid flow path constructed and arranged to be fluidically coupled to a chromatography column to receive sample from the chromatography column, the first tube coupled to a housing through a coupler constructed and arranged to couple the first tube to the housing without using a braze or weld.

In certain examples, the fluid flow path comprises a substantially inert material. In some examples, the first tube comprises a stainless steel and the substantially inert material is coated onto the stainless steel. In additional examples, the substantially inert material is a silica coating. In other examples, the fluid flow path comprises a non-catalytic metal material present in an effective amount to deter catalysis. In further examples, the fluid flow path comprises a non-catalytic, non-glass material present in an effective amount to deter catalysis. In certain embodiments, the fluid flow path comprises a substantially inert non-glass, non-stainless steel material. In additional embodiments, the fluid flow path comprises a non-catalytic metal oxide material present in an major amount to deter catalysis. In other embodiments, the fluid flow path comprises a substantially inert metal oxide material. In some embodiments, the fluid flow path comprises a non-catalytic metal material present in an effective amount to deter catalysis. In certain examples, the fluid flow path comprises a silica coating. In other examples, the coupler can be configured as a compressible ferrule. In some examples, the housing can include a second tube and a fitting, in which the second tube engages threads on the fitting to compress the ferrule and couple the first tube to the second tube.

Additional features, aspect, examples and embodiments are described in more detail below.

BRIEF DESCRIPTION OF THE FIGURES

Certain embodiments are described with reference to the figures in which.

Figure 1:
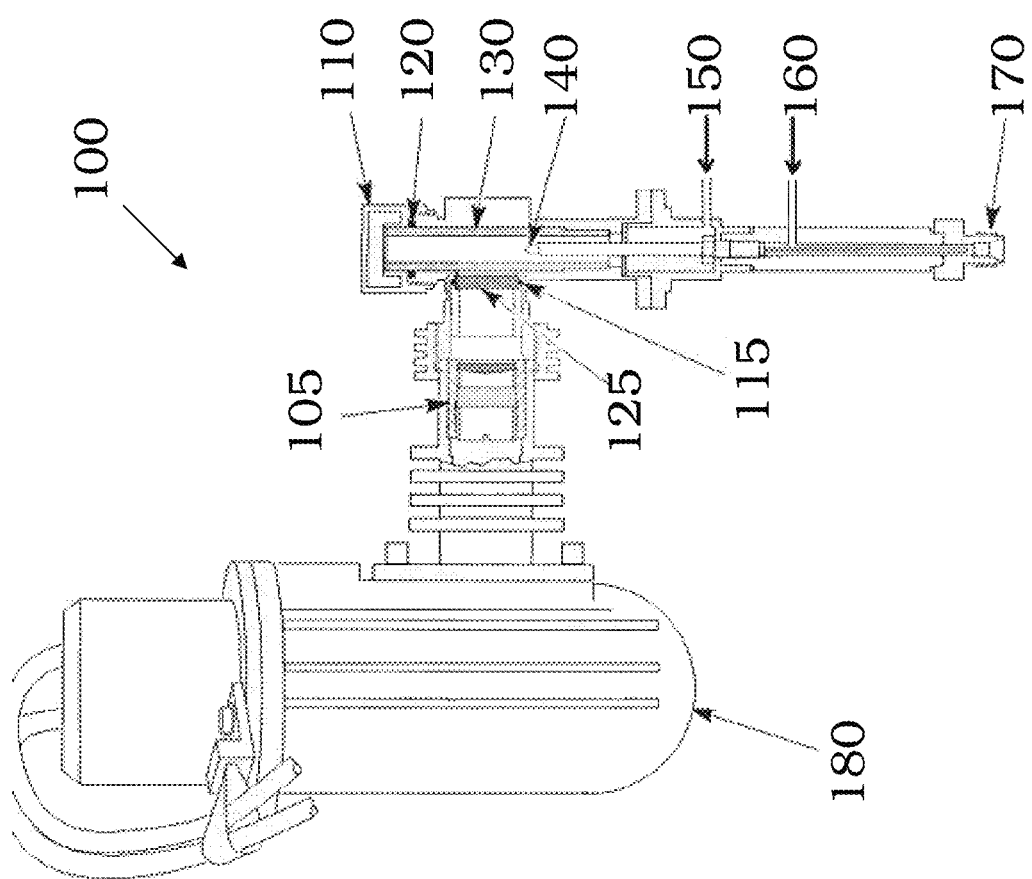
FIG. 1 is a cross-section of a flame photometric detector, in accordance with certain examples.

It will be recognized by the person of ordinary skill in the art, given the benefit of this disclosure, that certain dimensions or features in the figures may have been enlarged, distorted or shown in an otherwise unconventional or non-proportional manner to provide a more user friendly version of the figures. Where dimensions are specified in the description below, the dimensions are provided for illustrative purposes only.

DETAILED DESCRIPTION

Certain examples described herein are directed to jet assemblies that include one or more materials in a fluid flow path that can render at least some portion of fluid flow path substantially inert or non-catalytic. By including the substantially inert material on one or more surfaces of the jet assembly that are exposed to sample, the sample that contacts or resides near the surfaces should not react with the surfaces to a substantial degree or unwanted reactions are not substantially catalyzed by the surfaces. As described in more detail below, the particular type and amount of material on or in the fluid flow path (or other components of the jet assembly) can vary, and different types of materials may be desirably present to render the surface substantially inert.

In certain examples, the jet assemblies disclosed herein can be used with the injectors and injector inserts, if desired, that are described in U.S. 61/308,461. In addition, the jet assemblies can also be used with other devices and components commonly found in a chromatography system such as a gas chromatography system. Certain reference is made herein to one component being "inside" of another component. Where such reference is made, it is not intended to imply or mean that the entire component be inside the other component. Depending on the exact configuration of the device, all of one component may be positioned inside another component or a selected portion of one component may be positioned inside another component.

In certain embodiments, the entire jet assembly, if desired, can be produced from the substantially inert or non-catalytic materials. As described in more detail below, substantially inert materials are those materials that do not react with, catalyze or otherwise are affected by analytes in a sample stream. Non-catalytic materials are a materials that are not necessarily inert under all conditions, but they do not catalyze any reactions to a substantial degree under selected chromatographic conditions. For example, a non-catalytic material has suitable properties such that it does not catalyze any reaction to a substantial degree during the time a sample is resident or exposed to the surface of the jet assembly. There can be overlap of substantially inert materials and non-catalytic materials since substantially inert materials also do not catalyze reactions to any substantial degree no matter the residence time of the sample near the surface of the jet assembly. Specific types and amounts of each of the materials are described in more detail below. To reduce overall cost, it may be desirable to include the substantially inert or non-catalytic materials only on surfaces that contact the sample, and other portions of the jet assembly can be produced using conventional materials such as stainless steel. Illustrative types of materials that can be substantially inert and/or non-catalytic include but are not limited to titanium, titanium oxide, yttrium, yttrium oxide, aluminum, aluminum oxide, nickel, nickel alloys, chromium, chromium alloys, nickel chromium alloys and the like. Desirable nickel alloys include, but are not limited to, a Hastelloy® A alloy, a Hastelloy® B alloy, a Hastelloy® B2 alloy, a Hastelloy® B3 alloy, a Hastelloy® B142T alloy, a Hastelloy® Hybrid-BC1 alloy, a Hastelloy® C alloy, a Hastelloy® C4 alloy, a Hastelloy® C22 alloy, a Hastelloy® C22HS alloy, a Hastelloy® C2000 alloy, a Hastelloy® C263 alloy, a Hastelloy® C276 alloy, a Hastelloy® D alloy, a Hastelloy® G alloy, a Hastelloy® G2 alloy, a Hastelloy® G3 alloy, a Hastelloy® G30 alloy, a Hastelloy® G50 alloy, a Hastelloy® H9M alloy, a Hastelloy® N alloy, a Hastelloy® R235 alloy, a Hastelloy® S alloy, a Hastelloy® W alloy, a Hastelloy® X alloy and other Hastelloy® alloys or Haynes alloys commercially available from Haynes International, Inc. (Kokomo, Ind.). In some examples, the substantially inert material or the non-catalytic material can be a nickel-chromium alloy such as an Inconel® 600 alloy, an Inconel® 625 alloy, an Inconel® 718 alloy or other Inconel® alloys commercially available from Special Metals Corporation (New Hartford, N.Y.). Combinations of these various materials can also be used. One or more of these materials can be present on a surface of the jet assembly such that exposure of the sample to the surface does not result in any unwanted chemical reactions.

In certain embodiments, the substantially inert or non-catalytic materials can desirably be present on or in the fluid path of the jet assembly such as those used, for example in a flame photometric detector. Referring to FIG. 1, one illustration of a flame photometric detector (FPD) is shown. The flame photometric detector 100 includes an optical filter assembly 105, a cap 110, an O-ring 115, an I-ring 120, a window filter assembly 125, a glass liner 130, a flame jet 140, an air inlet 150, a hydrogen inlet 160, a column fitting 170 and a photomultiplier tube 180. It will be recognized by the person of ordinary skill in the art, given the benefit of this disclosure, that gases other than hydrogen can be introduced into the assembly and devices other than a photomultiplier tube can be used to receive a signal from the optical filter assembly 105. In operation of the FPD 100, sample effluent from the column is mixed with hydrogen gas. The mixture can then be burned in the presence of air in the flame jet 140. The FPD 100 is particularly useful for detecting sulfur, phosphorous, and tin compounds, which produce chemiluminescent reactions with emissions at wavelengths characteristic of the $S_2$ (or other sulfur species), Sn and HPo species. Trace amounts of liable reactive $S_2$ compounds can react with tubular internal metal parts of the stainless steel jet assembly. Heated metal part components will react with highly labile species such as hydrogen sulfide ($H_2S$). $H_2S$ will react with any unprotected internal jet assembly part resulting in loss of sample and unsatisfactory results in gas chromatography-FPD applications.

In certain examples, some ways to prevent undesired reactions in the jet assembly is to use sulfur resistant coating methods such as Sulfinert coating, inserting fused silica glass tubing into the jet, or adding gold plating to prevent loss of sample. While these coatings or materials can reduce losses, satisfactory performance is still not achieved with these methods in all cases. Sulfinert products are manufacturer recommended for maximum temperature use of 450 degrees Celsius, and it is difficult to uniformly coat a long small inner diameter tube such as required in a FPD jet construction. In addition, portions of the FPD jet assembly near the hydrogen air flame can surpass 450 degrees Celsius. Further, brazing or welding used in the jet assembly production process can compromise the coatings. Gold or other noble metal plating present the same type of limitations as for coatings; inadequate uniform plating of the long small inner tube diameter and temperature limitations near the flame as described for the inert coating processes. Additionally coatings and platings can degrade over time with temperature and exposure to chemicals. Use of fused silica tubes presents additional user steps at installation. The fused silica needs to be perfectly aligned to tip of the jet assembly. If placed slightly lower exposing any stainless steel surfaces then loss of samples will occur. If placed too high, it can interfere with the hydrogen air flame and add baseline noise to the chromatogram.

Figure 2:
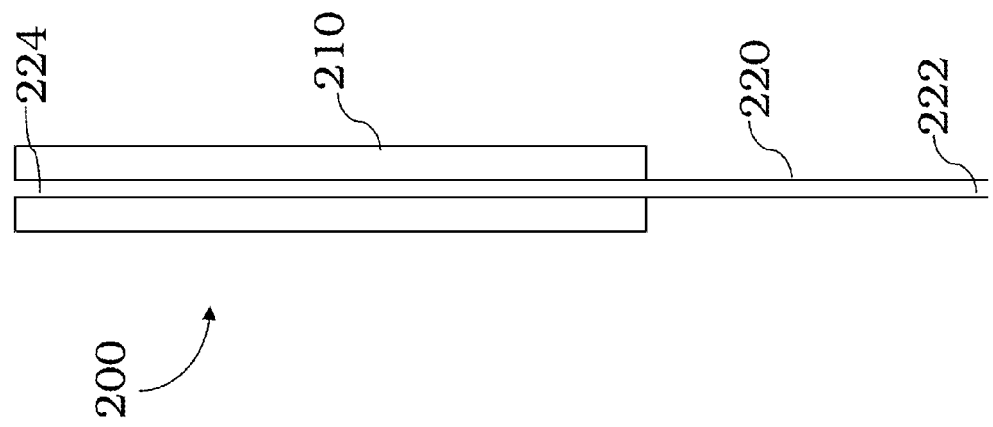
FIG. 2 is a cross-section of a jet assembly including a fluid flow path, in accordance with certain examples.

In certain embodiments, the jet assemblies described herein can include a substantially inert material or a non-catalytic material in a fluid flow path to prevent, or reduce the likelihood, of reaction of sample analyte with the jet assembly or to prevent catalysis of reactions by the jet assembly. A schematic of a jet assembly is shown in FIG. 2. The jet assembly 200 includes a housing 210 that surrounds or encloses a fluid flow path 220. In certain embodiments, the housing 210 can be produced using stainless steels or other materials since the housing 210 typically does not contact the sample. If desired, however, the housing 210 can be produced from the substantially inert and/or non-catalytic materials described herein. The housing 210 can include suitable fittings to permit coupling of the jet assembly 200 to other components of a flame photometric detector or other device where the jet assembly is to be used. The fluid flow path 220 can be entirely inside the housing 210, or as shown in FIG. 2, only a portion of the fluid flow path 210 can be in the housing 210. The fluid flow path typically is constructed and arranged such that it can be fluidically coupled to a chromatography column at an end 222 and can be fluidically coupled to a flame jet at an end 224. As sample exits from a column (not shown) it enters the fluid flow path 220 at the end 222. The sample can be mixed with air and hydrogen (or another combustion gas), and can then be burned in the flame to cause light emission of the sample. The emitted light can be detected and used to ascertain how much of a particular analyte is present. In some examples, the surfaces of the fluid flow path 220 can include a substantially inert material or a non-catalytic material. Such materials can be coated on, or, desirably, the entire fluid flow path can be formed from the substantially inert material or non-catalytic material such that unwanted interferences from coatings flaking off will not result.

In certain embodiments, the fluid flow path can be provided by producing a tube of the substantially inert material that can be coupled to a housing. For example, a tube comprising titanium can be produced with a hollow channel in the tube to provide a fluid flow path. The tube can be coupled to the housing using adhesives, welding, brazing or the like. In some examples, the tube can be inserted into the housing and can be brazed at a junction to the housing to retain the tube in place. The entire assembly can then be used as a jet assembly.

Figure 3:
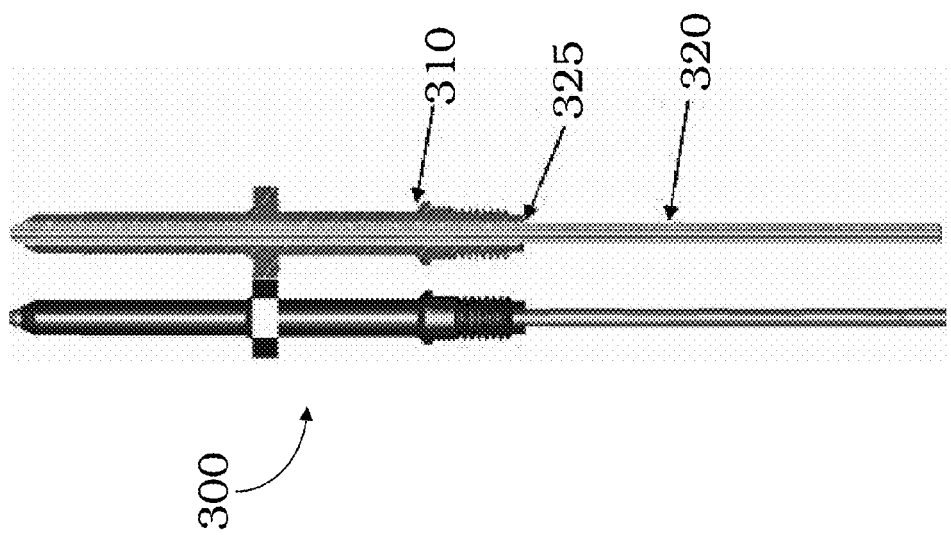
FIG. 3 is a schematic of a jet assembly including an outer tube and an inner tube, in accordance with certain examples.

In certain examples, the jet assembly can include an outer tube and an inner tube, where the inner tube provides the fluid flow path between a chromatography column and a flame jet. Referring to FIG. 3, an outer tube 310 is shown as surrounding an upper part of an inner tube 320. The inner tube 320 can be coupled to the outer tube 310 at a brazed junction 325, though other methods of joining the two tubes can be used. The entire inner tube 310 can be produced from a substantially inert material or a non-catalytic material to prevent unwanted reactions of the sample with surfaces of the inner tube.

In certain embodiments, the inner diameter of a tube that provides the fluid flow path can vary from about 0.015 inches to about 0.05 inches, e.g., about 0.028 to about 0.038 inches inner diameter. In some examples, the outer diameter of a tube that provides the fluid flow path can vary from about 0.02 inches to about 0.2 inches. The cross-sectional shape of the fluid flow path can vary and may be, for example, circular, elliptical, triangular, rectangular or take other shapes.

Figure 6:
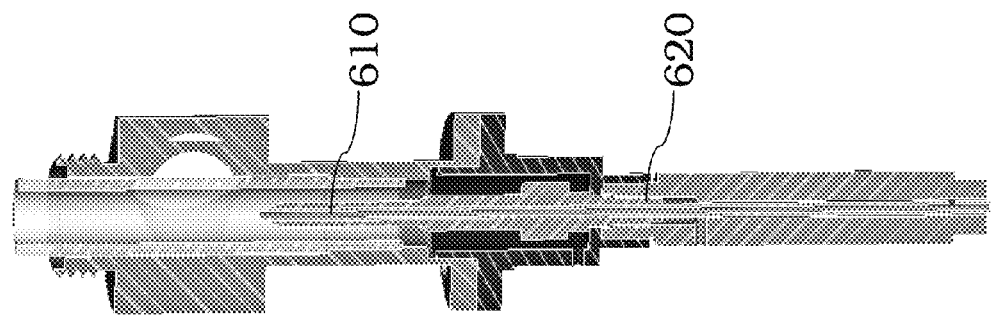
FIG. 6 is an illustration showing a jet assembly as part of a flame photometric detector, in accordance with certain examples.
Figure 5:
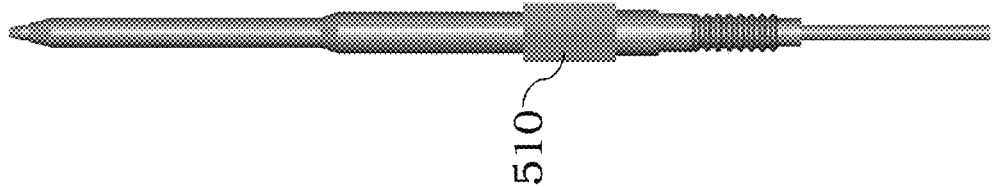
FIG. 5 is an illustration of a jet assembly that includes a fitting for securely coupling the jet assembly to a detector assembly, in accordance with certain examples.
Figure 4:
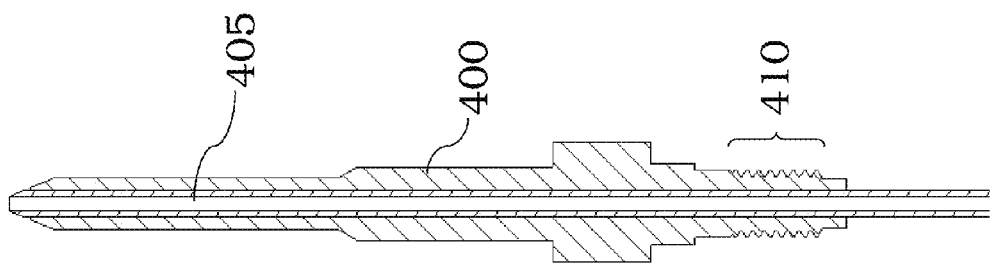
FIG. 4 is a cross-section of a jet assembly that includes external threads to couple to a detector assembly, in accordance with certain examples.

In some embodiments, the outer tube can include a suitable fitting or ferrule to couple to other devices. Referring to FIG. 4, a jet assembly housing 400 can include external threads 410 that can couple to internal threads of other components. In some embodiments, the coupling of the threads can effectuate a fluid tight seal such that fluid entering the fluid flow path 405 does not escape or leak into other parts of the system. In some examples and referring to FIG. 5, the housing can include a fitting 510 that can be engaged by a wrench or other tool a wrench to tighten and couple the jet assembly to another device. In addition, one or more gaskets, seals or the like can be included to assist in creation of a fluid tight seal, if desired. Referring to FIG. 6, a jet assembly 610 that includes a fluid flow path comprising a substantially inert material or a non-catalytic material is shown as being coupled to a flame photometric detector by mating the threads of the jet assembly 610 with threads 620 of the detector housing. If desired, sealing materials such as adhesives, thread lockers or the like can be used to retain the two components to each others.

Figure 7B:
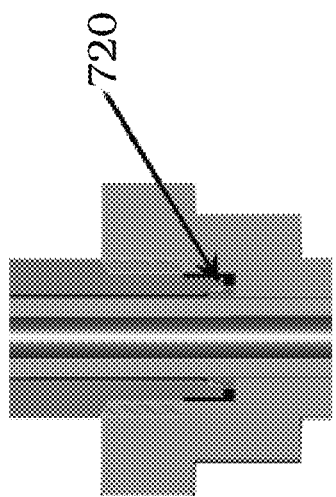
FIG. 7B is an expanded view of the coupler used to couple the inner and outer tubes of the jet assembly, in accordance with certain examples.
Figure 7A:
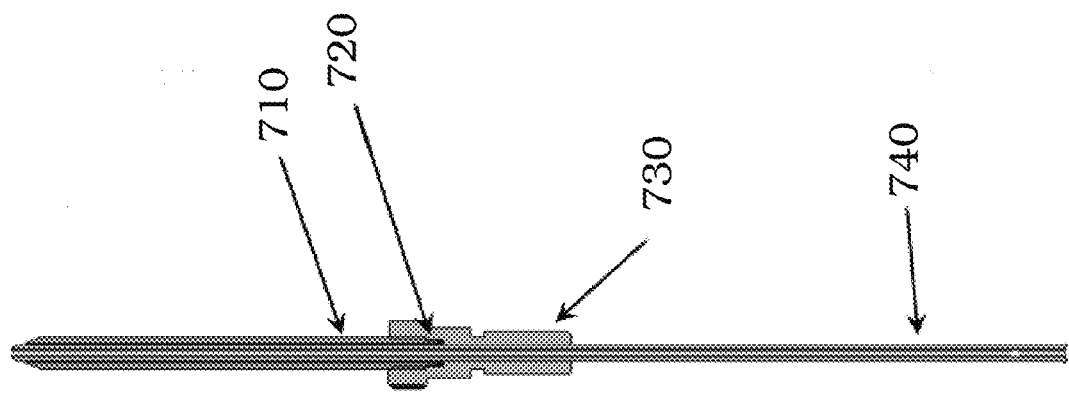
FIG. 7A is an illustration showing a brazeless or weldless jet assembly, in accordance with certain examples.

In certain embodiments, the jet assembly can be brazeless or weldless such that no braze or weld is present in the jet assembly to hold the inner and outer tubes together. Referring to FIGS. 7A and 7B, a jet assembly 700 includes an outer tube 710, an inner tube 740, a ferrule 720 and a threaded coupling 730. The inner tube 740 can be secured by the threads in the outer tube 710, which itself can be coupled to the threaded coupling 730. The coupling of the outer tube 710 to the threaded coupling 730 can act to compress the ferrule 720 in the region near the ferrule 720, as shown in FIG. 7B. In certain examples, this compression is operative to secure the inner tube 740 in a selected or fixed position in the jet assembly 700. In some examples, the inner tube 740 comprises one or more of the materials described herein, e.g., a substantially inert metal material, a non-catalytic metal material present in an effective amount to deter catalysis, a non-catalytic, non-glass material present in an effective amount to deter catalysis, a substantially inert non-glass, non-stainless steel material, a non-catalytic metal oxide material present in an major amount to deter catalysis, a substantially inert metal oxide material and combinations and derivatives thereof. In other examples, the inner tube 710 may include materials such as inert coatings, e.g., Sulfinert, etc. For example, the lack of brazing or welding in the jet assembly 700 permits the use of coatings that are typically compromised during the production steps of conventional jet assemblies. The brazeless or weldless embodiments described herein typically do not use high enough temperatures in the production process to effect the coatings. Such brazeless or weldless jet assemblies permit the inner tube to be comprised of other inert materials as well as solid metals and alloys, e.g., an inert coating on a stainless steel tube (for example, stainless steel 347 and the like), an inert coating on a substantially inert metal material, an inert coating on a non-catalytic metal material, an inert coating on a non-catalytic, non-glass material, a inert coating on a substantially inert non-glass, non-stainless steel material, an inert coating on a non-catalytic metal oxide material, an inert coating on a substantially inert metal oxide material, and combinations thereof. It will be within the ability of the person of ordinary skill in the art, given the benefit of this disclosure, to design and use suitable brazeless jet assemblies for an intended use.

In certain embodiments where a coating is present in a brazeless or weldless jet assembly, the coating may be, or may include, a silica coating including, but not limited to, a Sulfinert™ coating, a Siltek™ coating, a SilcoKlean™ coating, a SilcoGuard™ coating, a Silcolloy™ coating, a SilcoNert™ coating such as, for example, SilcoNert™ 1000 and SilcoNert™ 2000 coatings or other suitable coatings including but not limited to a borosilicate such as, for example, an extruded borosilicate. In some examples, a glass lined tube, e.g., a stainless steel glass lined tube can be used in the jet assembly or with the jet assembly. Suitable glass lined tubes will be readily selected by the person of ordinary skill in the art, given the benefit of this disclosure, and illustrative glass tubes may be obtained commercially from SGE Incorporated (Austin, Tex.).

Figure 8:
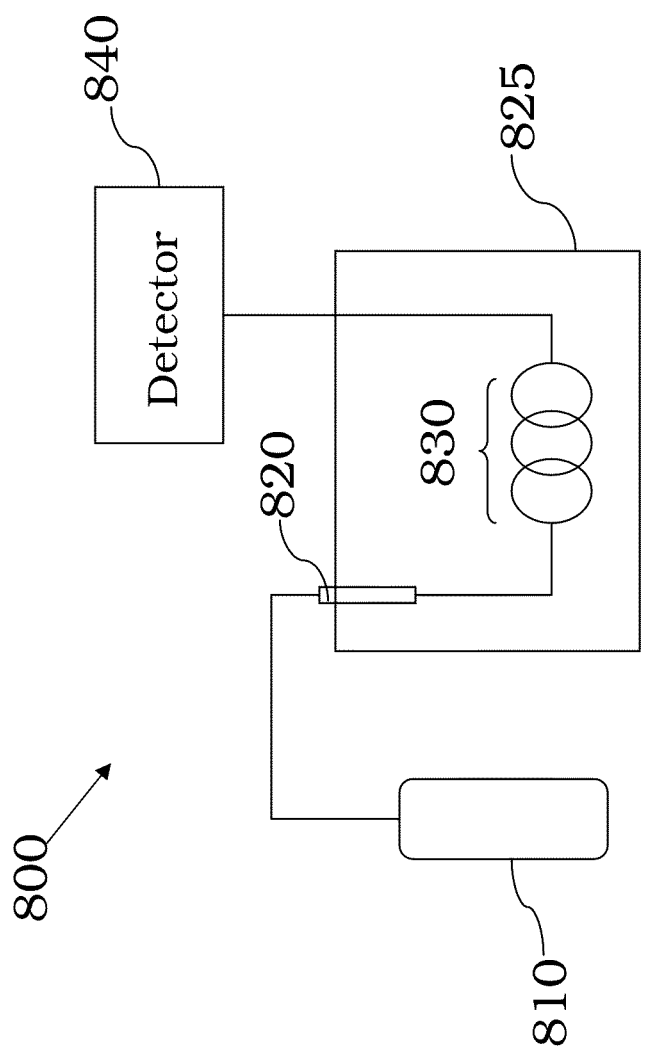
FIG. 8 is a schematic of a gas chromatography system, in accordance with certain examples.

In certain examples, an illustrative gas chromatography system that can include one or more of the devices described herein is shown in FIG. 8. The system 800 includes a carrier gas supply 810 fluidically coupled to an injector 820. The injector 820 can be fluidically coupled to a column 830, which includes a stationary phase selected to separate the analytes in a sample. The injector 820 is typically coupled to the column 830 through one or more ferrules or fittings to provide a fluid tight seal between the injector 820 and the column 830. The column 830 can take various forms and configurations including packed columns and open tubular or capillary columns. The column 830 can be housed in an oven 825, which is configured to implement one or more temperature profiles during the separation run. The column 830 can also be fluidically coupled to a detector 840. As analyte species elute from the column 830, the analyte species can be provided to the detector 840. The detector 840 can take various forms including, but not limited to a flame ionization detector, a thermal conductivity detector, a thermionic detector, a nitrogen phosphorous detector, an electron capture detector, an atomic emission detector, a flame photometric detector, a photoionization detector or a mass spectrometer. Where the detector takes the form of a mass spectrometer, a single mass spectrometer can be present or multiple mass spectrometers can be present. If desired, surfaces of these detectors that come into contact with the sample can include a substantially inert material or a non-catalytic material as described herein. For example, it may be desirable to include a tube comprising a fluid flow path that is substantially inert in a flame ionization detector, a nitrogen phosphorous detector or other detectors to reduce the likelihood that hot surfaces of the detectors will react with or catalyze a reaction. In use of the system 800 shown in FIG. 8, the temperature of the oven 825 may be raised to a starting temperature to permit the column 830 to warm up to that temperature. A sample can be injected through the injector 820. Carrier gas from the gas source 810 will sweep the sample into the fluid flow path of the injector 820. Sample can enter the column 830 where it will be separated into individual analytes. These separated analytes will elute from the column 830 and be provided to the detector 840 for detection. Where a FPD detector is used, the sample can pass through a fluid flow path comprising a substantially inert material or a non-catalytic material prior to or after being mixed with air and a gas such as hydrogen. The burned sample can emit light which is detected by optics and/or electronics in the detector. Where a flame ionization detector (FID) is used, the sample can be burned and ionized, and the resulting current can be measured. A nitrogen-phosphorous detector (NPD) operates similar to an FID, but is more sensitive toward phosphorous and nitrogen compounds. The NPD detector can measure large ion currents produced in the presence of phosphorous and nitrogen compounds. Other detectors that include a jet assembly or a flame may particularly benefit by the inclusion of a fluid flow path comprising a substantially inert or non-catalytic material.

In certain embodiments, a jet assembly for use in a detector can include a fluid flow path in a housing, in which the fluid flow path is constructed and arranged to be fluidically coupled to a chromatography column to receive sample from the chromatography column, and in which the fluid flow path comprises a substantially inert metal material. In some examples, the detector can be a FPD, a FID or a NPD or other detector. In certain embodiments, the substantially inert metal material can be present in a major amount. In some examples, the substantially inert metal material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof. In some examples, the substantially inert metal material is present in a non-coated form. In other examples, the substantially inert metal material is in a tube that is integral to the housing.

In other embodiments, a jet assembly can include a fluid flow path in a housing, in which the fluid flow path is constructed and arranged to be fluidically coupled to a chromatography column to receive sample from the chromatography column, and in which the fluid flow path comprises a non-catalytic metal material present in an effective amount to deter catalysis in the fluid flow path. In some embodiments, the detector can be a FPD, a FID or a NPD or other detector. In certain embodiments, the non-catalytic metal material is present in a major amount. In other embodiments, the non-catalytic metal material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof. In some embodiments, the non-catalytic metal material is present in a non-coated form. In other embodiments, the non-catalytic metal material is in a tube that is integral to the housing.

In certain examples, a jet assembly that includes a first tube and a second tube can be used. In some examples, the first tube can be configured to couple to a detector assembly. In other examples, the second tube can be inside the first tube, in which the second tube comprises a fluid flow path that is constructed and arranged to be fluidically coupled to a chromatography column to receive sample from the chromatography column, and in which the fluid flow path comprises a non-catalytic metal material present in an effective amount to deter catalysis in the fluid flow path. In some examples, the detector assembly can be a FPD, a FID or a NPD assembly or other detector assembly. In certain examples, the non-catalytic metal material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof. In some examples, the non-catalytic metal material is present in a non-coated form. In other examples, the second tube is longer than the first tube to fluidically couple to the chromatography column. In additional examples, the first tube comprises a non-catalytic material.

In certain embodiments, a jet assembly can be used that includes a first tube configured to couple to a detector assembly, and a second tube inside the first tube, in which the second tube comprises a fluid flow path that is constructed and arranged to be fluidically coupled to a chromatography column to receive sample from the chromatography column, and in which the fluid flow path comprises a major amount of a substantially inert metal material. In some embodiments, the detector assembly can be a FPD, a FID or a NPD assembly or other detector assembly. In other embodiments, the substantially inert metal material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof. In certain embodiments, the substantially inert metal material is present in a non-coated form. In other embodiments, the second tube is longer than the first tube to fluidically couple to the chromatography column. In additional embodiments, the first tube comprises a substantially inert metal material.

In certain examples, a jet assembly can be used that includes a fluid flow path inside a housing, in which the fluid flow path comprises a non-catalytic, non-glass material present in an effective amount to deter catalysis. In some examples, the jet assembly can be used in a FPD, a FID or a NPD or other detector. In other examples, the non-catalytic, non-glass material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof. In certain examples, the non-catalytic, non-glass material is present in a non-coated form. In other examples, the non-catalytic, non-glass material is in a tube that is integral to the housing. In some examples, the housing is configured as a first tube.

In certain embodiments, a jet assembly can be used that includes a fluid flow path inside a housing, in which the fluid flow path comprises, in which the fluid flow path comprises a substantially inert non-glass, non-stainless steel material. In some embodiments, the jet assembly can be used in a FPD, a FID or a NPD or other detector. In other embodiments, the substantially inert non-glass, non-stainless steel material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof. In additional examples, the substantially inert non-glass, non-stainless steel material is present in a non-coated form. In some examples, the substantially inert non-glass, non-stainless steel material is in a tube that is integral to the housing. In other examples, the housing is configured as a first tube.

In certain examples, a jet assembly insert can be used that is constructed and arranged to couple to a housing of a jet assembly, the jet assembly insert comprising a fluid flow path that is configured to be fluidically coupled to a chromatography column, in which the fluid flow path comprises a substantially inert metal material. In some embodiments, the jet assembly insert can be used in a FPD, a FID or a NPD or other detector. In other examples, the substantially inert metal material is present in a major amount. In some examples, the substantially inert metal material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In certain embodiments, a jet assembly insert can be used that is constructed and arranged to couple to a housing of a jet assembly, the jet assembly insert comprising a fluid flow path that is configured to be fluidically coupled to a chromatography column, in which the fluid flow path of comprises a non-catalytic metal material present in an effective amount to deter catalysis in the fluid flow path. In some examples, the jet assembly insert can be used in a FPD, a FID or a NPD or other detector. In other embodiments, the non-catalytic metal material is present in a major amount. In certain embodiments, the non-catalytic metal material titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In certain examples, a jet assembly insert can be used that is constructed and arranged to couple to a housing of a jet assembly, the jet assembly insert comprising a fluid flow path that is configured to be fluidically coupled to a chromatography column, in which the fluid flow path comprises a non-catalytic metal oxide material present in an major amount to deter catalysis. In some examples, the jet assembly insert can be used in a FPD, a FID or a NPD or other detector. In other examples, the non-catalytic metal oxide material is present in a major amount. In some examples, the non-catalytic metal oxide material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In certain embodiments, a jet assembly insert can be used that is constructed and arranged to couple to a housing of a jet assembly, the jet assembly insert comprising a fluid flow path that is configured to be fluidically coupled to a chromatography column, in which the fluid flow path comprises a substantially inert metal oxide material. In some embodiments, the jet assembly insert can be used in a FPD, a FID or a NPD or other detector. In other embodiments, the substantially inert metal oxide material is present in a major amount. In some embodiments, the substantially inert metal oxide material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In certain examples, a flame detector can be used that includes a flame jet, and a fluid flow path that is constructed and arranged to be fluidically coupled to a chromatography column at one end and to the flame jet at an opposite end, the fluid flow path comprising a substantially inert metal material. In some embodiments, the flame detector can be a FPD, a FID or a NPD or other detector. In certain embodiments, the substantially inert metal material is present in a major amount. In other examples, the substantially inert metal material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In certain embodiments, a flame detector can be used that includes a flame jet, and a fluid flow path that is constructed and arranged to be fluidically coupled to a chromatography column at one end and to the flame jet at an opposite end, the fluid flow path comprising a non-catalytic metal material present in an effective amount to deter catalysis in the fluid flow path. In some embodiments, the flame detector can be a FPD, a FID or a NPD or other detector. In other embodiments, the non-catalytic metal material is present in a major amount. In additional embodiment, the non-catalytic metal material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In certain examples, a flame detector can include a flame jet, and a fluid flow path that is constructed and arranged to be fluidically coupled to a chromatography column at one end and to the flame jet at an opposite end, the fluid flow path comprising a substantially inert metal oxide material. In some examples, the flame detector can be a FPD, a FID or a NPD or other detector. In other examples, the substantially inert metal oxide material is present in a major amount. In certain examples, the substantially inert metal oxide material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In certain embodiments, a flame detector can include a flame jet, and a fluid flow path that is constructed and arranged to be fluidically coupled to a chromatography column at one end and to the flame jet at an opposite end, the fluid flow path comprising a non-catalytic metal oxide material present in an major amount to deter catalysis. In other embodiments, the flame detector can be a FPD, a FID or a NPD or other detector. In some embodiments, the non-catalytic metal oxide material is present in a major amount. In additional embodiments, the non-catalytic metal oxide material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In certain examples, a flame detector can include a flame jet, and a fluid flow path that is constructed and arranged to be fluidically coupled to a chromatography column at one end and to the flame jet at an opposite end, the fluid flow path comprising a non-catalytic, non-glass material present in an effective amount to deter catalysis. In other examples, the flame detector can be a FPD, a FID or a NPD or other detector. In some examples, the non-catalytic, non-glass material is present in a major amount. In additional examples, the non-catalytic, non-glass material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In certain embodiments, a flame detector can include a flame jet, and a fluid flow path that is constructed and arranged to be fluidically coupled to a chromatography column at one end and to the flame jet at an opposite end, the fluid flow path comprising a substantially inert non-glass, non-stainless steel material. In other embodiments, the flame detector can be a FPD, a FID or a NPD or other detector. In some embodiments, the substantially inert non-glass, non-stainless steel material is present in a major amount. In additional embodiments, the substantially inert non-glass, non-stainless steel material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In some examples, a kit can include a jet assembly for use in a flame detector, the jet assembly comprising a fluid flow path in a housing, in which the fluid flow path is constructed and arranged to be fluidically coupled to a chromatography column to receive sample from the chromatography column, and in which the fluid flow path comprises a substantially inert metal material. In additional examples, the substantially inert metal material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In other examples, a kit can include a jet assembly for use in a flame detector, the jet assembly comprising a fluid flow path in a housing, in which the fluid flow path is constructed and arranged to be fluidically coupled to a chromatography column to receive sample from the chromatography column, and in which the fluid flow path comprises a non-catalytic metal material present in an effective amount to deter catalysis in the fluid flow path. In some examples, the non-catalytic metal material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In additional examples, a kit can include a jet assembly comprising a first tube configured to couple to a flame photometric detector assembly, and a second tube inside the first tube, in which the second tube comprises a fluid flow path that is constructed and arranged to be fluidically coupled to a chromatography column to receive sample from the chromatography column, and in which the fluid flow path comprises a non-catalytic metal material present in an effective amount to deter catalysis in the fluid flow path. In some examples, the non-catalytic metal material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In some examples, a kit can include a jet assembly comprising a first tube configured to couple to a flame photometric detector assembly, and a second tube inside the first tube, in which the second tube comprises a fluid flow path that is constructed and arranged to be fluidically coupled to a chromatography column to receive sample from the chromatography column, and in which the fluid flow path comprises a major amount of a substantially inert metal material. In other examples, the substantially inert metal material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In certain examples, a kit can include a jet assembly comprising a fluid flow path inside a housing, in which the fluid flow path comprises a non-catalytic, non-glass material present in an effective amount to deter catalysis. In some examples, the non-catalytic, non-glass material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In other examples, a kit can include a jet assembly comprising a fluid flow path inside a housing, in which the fluid flow path comprises, in which the fluid flow path comprises a substantially inert non-glass, non-stainless steel material. In certain examples, the non-glass, non-stainless steel material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In additional examples, a kit can include a jet assembly insert that is constructed and arranged to couple to a housing of a jet assembly, the jet assembly insert comprising a fluid flow path that is configured to be fluidically coupled to a chromatography column, in which the fluid flow path comprises a substantially inert metal material. In other examples, the substantially inert metal material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In further examples, a kit can include a jet assembly insert that is constructed and arranged to couple to a housing of a jet assembly, the jet assembly insert comprising a fluid flow path that is configured to be fluidically coupled to a chromatography column, in which the fluid flow path of comprises a non-catalytic metal material present in an effective amount to deter catalysis in the fluid flow path. In other examples, the non-catalytic metal material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In some embodiments, a kit can include a jet assembly insert that is constructed and arranged to couple to a housing of a jet assembly, the jet assembly insert comprising a fluid flow path that is configured to be fluidically coupled to a chromatography column, in which the fluid flow path comprises a non-catalytic metal oxide material present in an major amount to deter catalysis. In other examples, the non-catalytic metal oxide material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In other embodiments, a kit can include a jet assembly insert that is constructed and arranged to couple to a housing of a jet assembly, the jet assembly insert comprising a fluid flow path that is configured to be fluidically coupled to a chromatography column, in which the fluid flow path comprises a substantially inert metal oxide material. In other examples, the substantially inert metal oxide material comprises titanium, aluminum, yttrium, titanium oxide, aluminum oxide, yttrium oxide, nickel, chromium, a Hastelloy® alloy, an Inconel® alloy, other alloys commonly available from Haynes International, Inc. or combinations thereof.

In additional embodiments, a kit can include a flame detector comprising a flame jet, and a fluid flow path that is constructed and arranged to be fluidically coupled to a chromatography column at one end and to the flame jet at an opposite end, the fluid flow path comprising a substantially inert metal material. In other embodiments, the flame detector can be a FPD, a FID or a NPD or other detector.

In some embodiments, a kit can include a flame detector comprising a flame jet, and a fluid flow path that is constructed and arranged to be fluidically coupled to a chromatography column at one end and to the flame jet at an opposite end, the fluid flow path comprising a non-catalytic metal material present in an effective amount to deter catalysis in the fluid flow path. In other embodiments, the flame detector can be a FPD, a FID or a NPD or other detector.

In certain examples, a kit can include a flame detector comprising a flame jet, and a fluid flow path that is constructed and arranged to be fluidically coupled to a chromatography column at one end and to the flame jet at an opposite end, the fluid flow path comprising a substantially inert metal oxide material. In other examples, the flame detector can be a FPD, a FID or a NPD or other detector.

In certain embodiments, a kit can include a flame detector comprising a flame jet, and a fluid flow path that is constructed and arranged to be fluidically coupled to a chromatography column at one end and to the flame jet at an opposite end, the fluid flow path comprising a non-catalytic metal oxide material present in an major amount to deter catalysis. In certain examples, the flame detector can be a FPD, a FID or a NPD or other detector.

In some embodiments, a kit can include a flame detector comprising a flame jet, and a fluid flow path that is constructed and arranged to be fluidically coupled to a chromatography column at one end and to the flame jet at an opposite end, the fluid flow path comprising a non-catalytic, non-glass material present in an effective amount to deter catalysis. In certain embodiments, the flame detector can be a FPD, a FID or a NPD or other detector.

In other embodiments, a kit can include a flame detector comprising a flame jet, and a fluid flow path that is constructed and arranged to be fluidically coupled to a chromatography column at one end and to the flame jet at an opposite end, the fluid flow path comprising a substantially inert non-glass, non-stainless steel material. In some examples, the flame detector can be a FPD, a FID or a NPD or other detector.

In certain embodiments, a method of facilitating chromatographic analysis includes providing a jet assembly comprising a fluid flow path in a housing, in which the fluid flow path is constructed and arranged to be fluidically coupled to a chromatography column to receive sample from the chromatography column, and in which the fluid flow path comprises a substantially inert metal material.

In other embodiments, a method of facilitating chromatographic analysis can include providing a jet assembly comprising a fluid flow path in a housing, in which the fluid flow path is constructed and arranged to be fluidically coupled to a chromatography column to receive sample from the chromatography column, and in which the fluid flow path comprises a non-catalytic metal material present in an effective amount to deter catalysis in the fluid flow path.

In additional embodiments, a method of facilitating chromatographic analysis can include providing a jet assembly comprising a first tube configured to couple to a flame detector assembly, and a second tube inside the first tube, in which the second tube comprises a fluid flow path that is constructed and arranged to be fluidically coupled to a chromatography column to receive sample from the chromatography column, and in which the fluid flow path comprises a non-catalytic metal material present in an effective amount to deter catalysis in the fluid flow path.

In some embodiments, a method of facilitating chromatographic analysis can include providing a jet assembly comprising a first tube configured to couple to a flame detector assembly, and a second tube inside the first tube, in which the second tube comprises a fluid flow path that is constructed and arranged to be fluidically coupled to a chromatography column to receive sample from the chromatography column, and in which the fluid flow path comprises a major amount of a substantially inert metal material.

In certain examples, a method of facilitating chromatographic analysis can include providing a jet assembly comprising a fluid flow path inside a housing, in which the fluid flow path comprises a non-catalytic, non-glass material present in an effective amount to deter catalysis.

In other examples, a method of facilitating chromatographic analysis can include providing a jet assembly comprising a fluid flow path inside a housing, in which the fluid flow path comprises, in which the fluid flow path comprises a substantially inert non-glass, non-stainless steel material.

In additional examples, a method of facilitating chromatographic analysis can include providing a jet assembly insert that is constructed and arranged to couple to a housing of a jet assembly, the jet assembly insert comprising a fluid flow path that is configured to be fluidically coupled to a chromatography column, in which the fluid flow path comprises a substantially inert metal material.

In some examples, a method of facilitating chromatographic analysis can include providing a jet assembly insert that is constructed and arranged to couple to a housing of a jet assembly, the jet assembly insert comprising a fluid flow path that is configured to be fluidically coupled to a chromatography column, in which the fluid flow path of comprises a non-catalytic metal material present in an effective amount to deter catalysis in the fluid flow path.

In further examples, a method of facilitating chromatographic analysis can include providing a jet assembly insert that is constructed and arranged to couple to a housing of a jet assembly, the jet assembly insert comprising a fluid flow path that is configured to be fluidically coupled to a chromatography column, in which the fluid flow path comprises a non-catalytic metal oxide material present in an major amount to deter catalysis.

In certain embodiments, a method of facilitating chromatographic analysis can include providing a jet assembly insert that is constructed and arranged to couple to a housing of a jet assembly, the jet assembly insert comprising a fluid flow path that is configured to be fluidically coupled to a chromatography column, in which the fluid flow path comprises a substantially inert metal oxide material.

In other embodiments, a method of facilitating chromatographic analysis can include providing a flame detector comprising a flame jet, and a fluid flow path that is constructed and arranged to be fluidically coupled to a chromatography column at one end and to the flame jet at an opposite end, the fluid flow path comprising a substantially inert metal material.

In additional embodiments, a method of facilitating chromatographic analysis can include providing a flame detector comprising a flame jet, and a fluid flow path that is constructed and arranged to be fluidically coupled to a chromatography column at one end and to the flame jet at an opposite end, the fluid flow path comprising a non-catalytic metal material present in an effective amount to deter catalysis in the fluid flow path.

In certain examples, a method of facilitating chromatographic analysis can include providing a flame detector comprising a flame jet, and a fluid flow path that is constructed and arranged to be fluidically coupled to a chromatography column at one end and to the flame jet at an opposite end, the fluid flow path comprising a substantially inert metal oxide material.

In other examples, a method of facilitating chromatographic analysis can include providing a flame detector comprising a flame jet, and a fluid flow path that is constructed and arranged to be fluidically coupled to a chromatography column at one end and to the flame jet at an opposite end, the fluid flow path comprising a non-catalytic metal oxide material present in an major amount to deter catalysis.

In some examples, a method of facilitating chromatographic analysis can include providing a flame photometric detector comprising a flame jet, and a fluid flow path that is constructed and arranged to be fluidically coupled to a chromatography column at one end and to the flame jet at an opposite end, the fluid flow path comprising a non-catalytic, non-glass material present in an effective amount to deter catalysis.

In additional examples, a method of facilitating chromatographic analysis can include providing a flame photometric detector comprising a flame jet, and a fluid flow path that is constructed and arranged to be fluidically coupled to a chromatography column at one end and to the flame jet at an opposite end, the fluid flow path comprising a substantially inert non-glass, non-stainless steel material.

In certain embodiments of the jet assemblies, the fluid flow paths can include titanium, yttrium, aluminum, nickel, chromium, a nickel alloy, a chromium alloy, a nickel chromium alloy, Hastelloy® alloys, Inconel® alloys, combinations thereof, or other materials. Certain specific examples are described below to illustrate further the novel technology described herein Example 1

Figure 9:
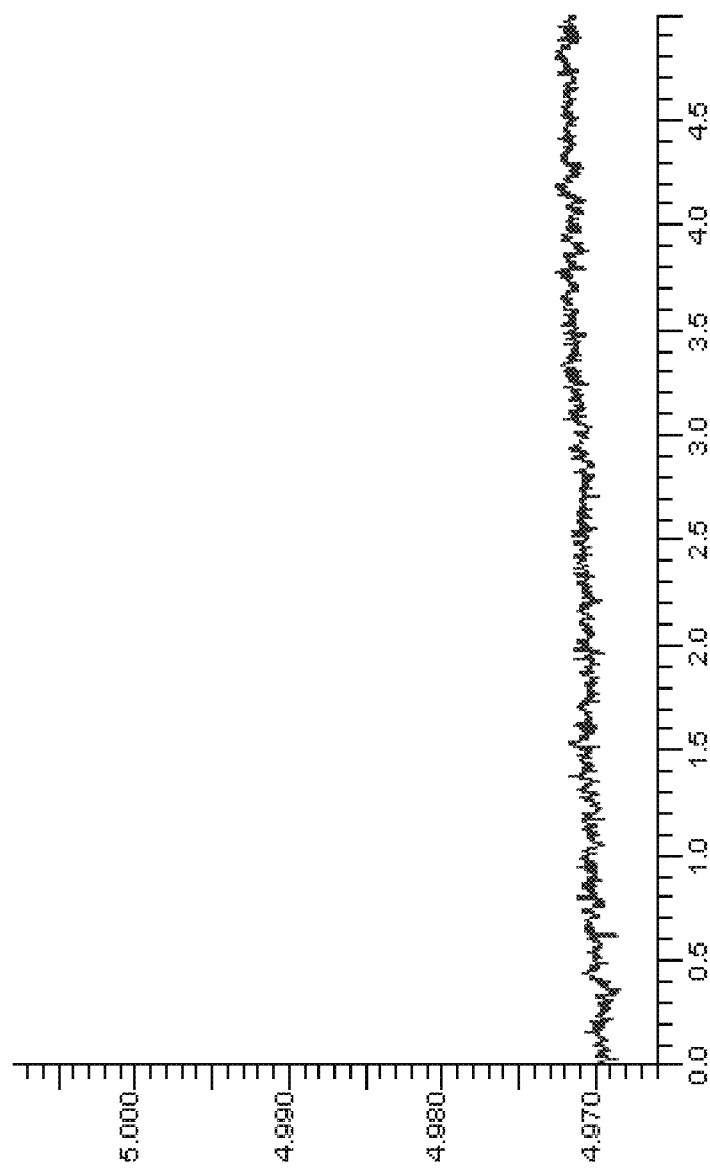
FIG. 9 is a chromatogram showing the absence of hydrogen sulfide when a conventional stainless steel fluid flow path is present in a jet assembly, in accordance with certain examples.
Figure 10:
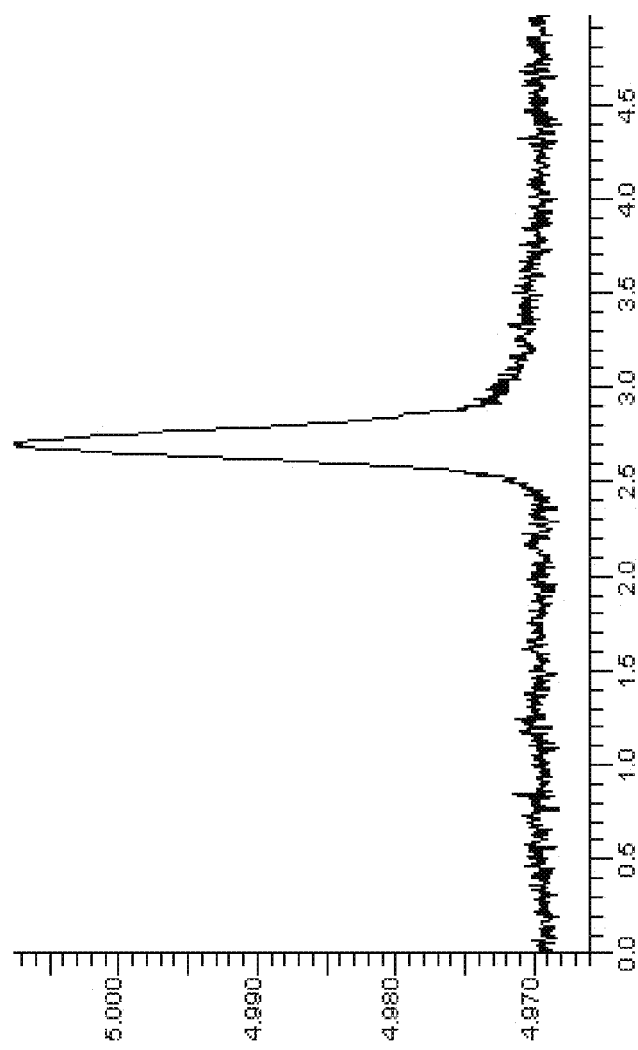
FIG. 10 is a chromatogram showing the presence of hydrogen sulfide when a titanium fluid flow path is present in a jet assembly, in accordance with certain examples.

A flame photometric detector including a jet assembly with a conventional stainless steel fluid flow path was compared a flame photometric detector including a jet assembly with a titanium flow path. The titanium flow path was provided using a titanium inner tube that was inserted into the housing and brazed at a single site. The test equipment was a Kin-Tek Model 491-MB gas standards generator, and a VICI gas sampling valve injecting 1 ppm of Hydrogen sulfide gas was used to test the recovery. The gas sampling valve was connected to a Perkin Elmer model Clarus 500 Gas Chromatograph equipped with an FPD detector and programmable pneumatic control. The sample including hydrogen sulfide ($H_2S$) was injected and analyzed using each of the FPD detectors. Where the conventional jet assembly was present, the $H_2S$ peak was absent (see FIG. 9). $H_2S$ appeared to react with the stainless steel in the conventional jet assembly. Where the titanium fluid flow path was present, the $H_2S$ peak was observed (see FIG. 10), thus confirming that a substantially inert fluid flow path is suitable for use with species such as $H_2S$.

Example 2

A brazeless jet assembly was tested for its ability to recover $H_2S$. The test equipment was a Kin-Tek Model 491-MB gas standards generator, and a VICI gas sampling valve injecting 1 ppm of Hydrogen sulfide gas was used to test the recovery. The gas sampling valve was connected to a Perkin Elmer model Clarus 500 Gas Chromatograph equipped with an FPD detector and programmable pneumatic control.

Figure 11A:
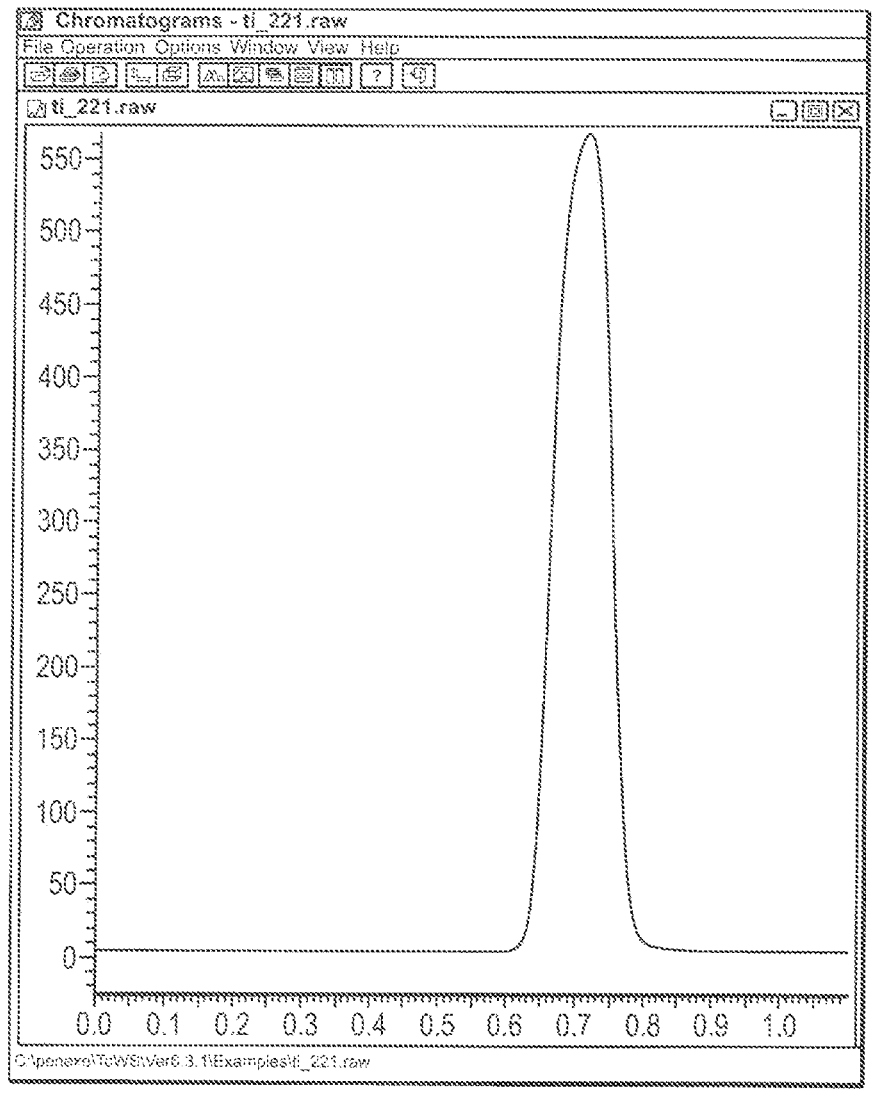
FIG. 11A is chromatogram of $H_2S$ using a brazeless jet assembly including a fused capillary insert.

A jet assembly was tested first with a fused silica capillary tube installed all the way to the top of the jet assembly flush with the tip of the jet. The inner tube was produced using titanium. The $H_2S$ sample would travel out of the fused silica column without any exposure to the steel jet assembly. This configuration should yield the maximum ideal response for $H_2S$. The $H_2S$ sample is not exposed to any metal surface of the jet assembly avoiding any reaction and not incurring any substantial loss of $H_2S$ sample. The results using this fused silica capillary tube were used as a control for the comparison of the percent recovery for $H_2S$. The $H_2S$ FPD chromatogram response was recorded in the form of peak area (FIG. 11A).

Figure 11B:
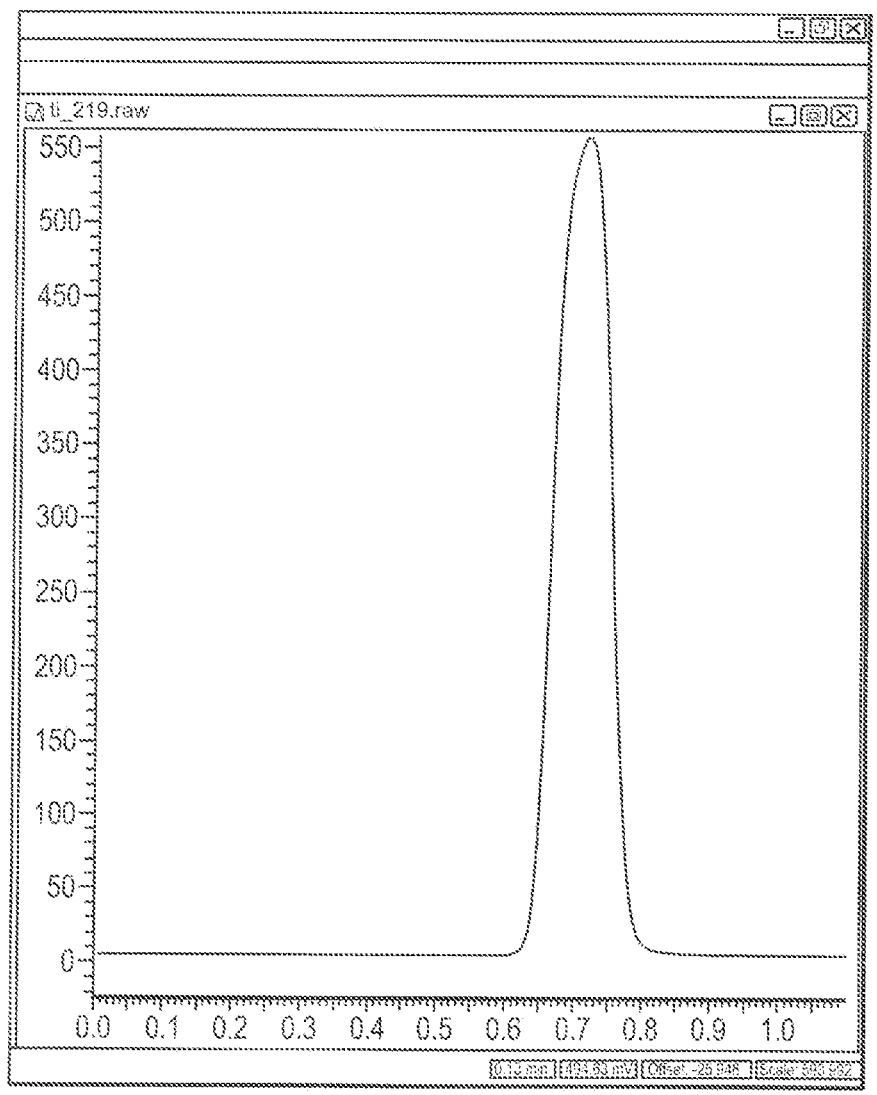
FIG. 11B is a chromatogram of $H_2S$ using a brazeless jet assembly without the insert, in accordance with certain examples.
Figure 12:
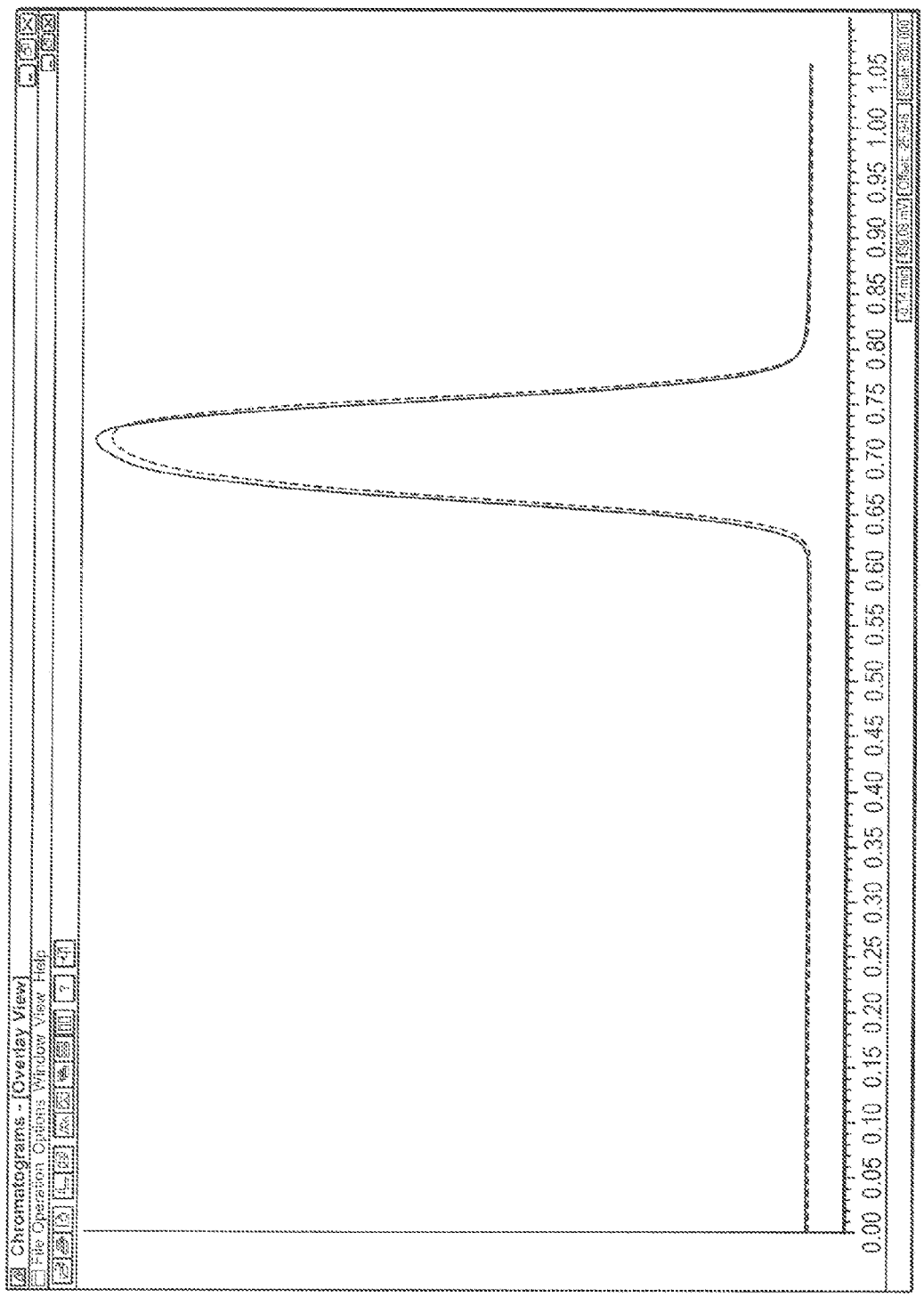
FIG. 12 is an overlay chromatogram of the chromatograms of FIGS. 11A and 11B, in accordance with certain examples.

The fused silica capillary tube was then removed from the jet assembly allowing the $H_2S$ sample to be exposed to and travel inside the length of the jet assembly. The $H_2S$ FPD chromatogram response again is recorded in the form of peak area (FIG. 11B). The chromatograms were overlaid for comparison, as shown in FIG. 12. The recovery was then calculated as percentage of peak area response (fused silica to top of jet) divided by peak area response (no fused silica) times 100. A good recovery result will yield a minimum 90% or greater. The calculated recovery was greater than 90%.

Figure 13A:
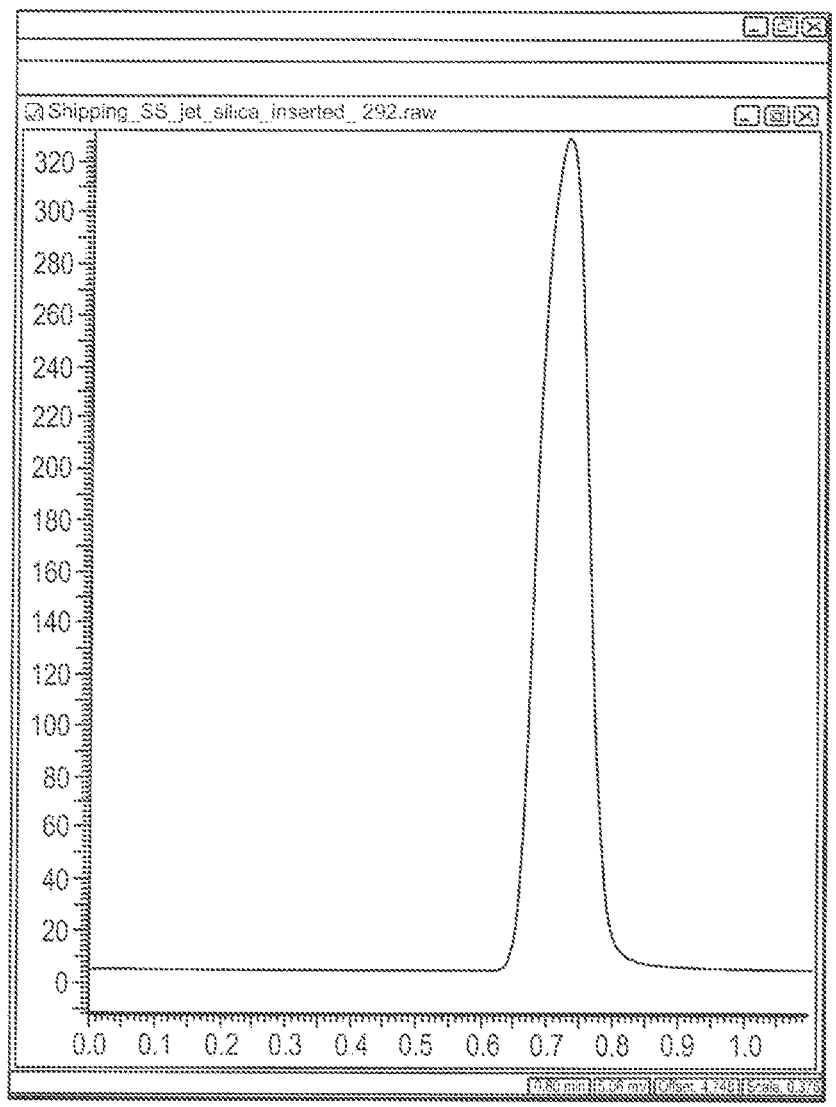
FIG. 13A is a chromatogram of $H_2S$ using a fused capillary insert with a jet assembly having a stainless steel fluid flow path.
Figure 13B:
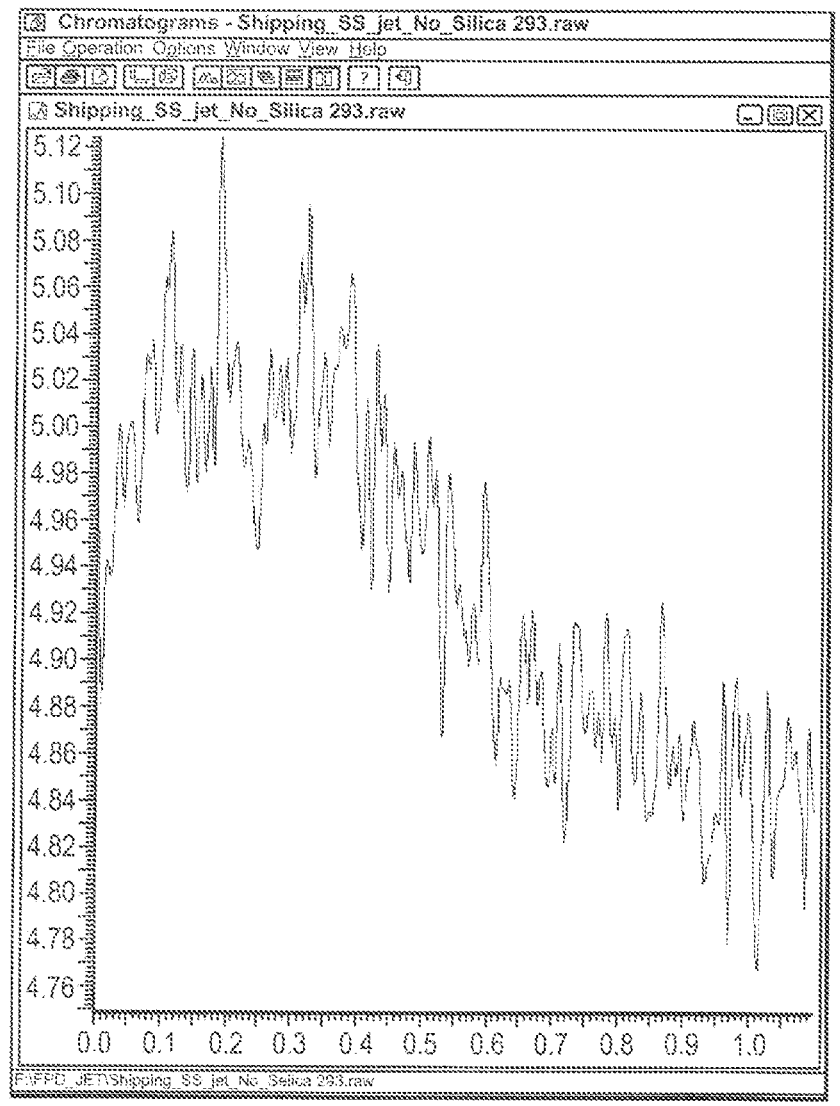
FIG. 13B is a chromatogram showing no recovery of $H_2S$ when the fused capillary insert is removed, in accordance with certain examples.

For comparison purposes, a similar experiment was conducted using a stainless steel jet assembly. An $H_2S$ response is shown in FIG. 13A, where the stainless steel jet assembly included a fused silica insert. When the fused silica inert was removed from the jet assembly, there was no to minimal response and no recovery of the $H_2S$ (FIG. 13B). All $H_2S$ sample was lost due to exposure to the unprotected stainless steel jet body.

Example 3

A jet assembly was produced from a 1/16 inch outer diameter, 0.034 inch inner diameter swaged inner tube. The inner jet tube was produced using 347 anticorrosion stainless steel (High Nickel, Chromium content, doped with tantalum) and was coated with Silconert-2000.

Figure 14A:
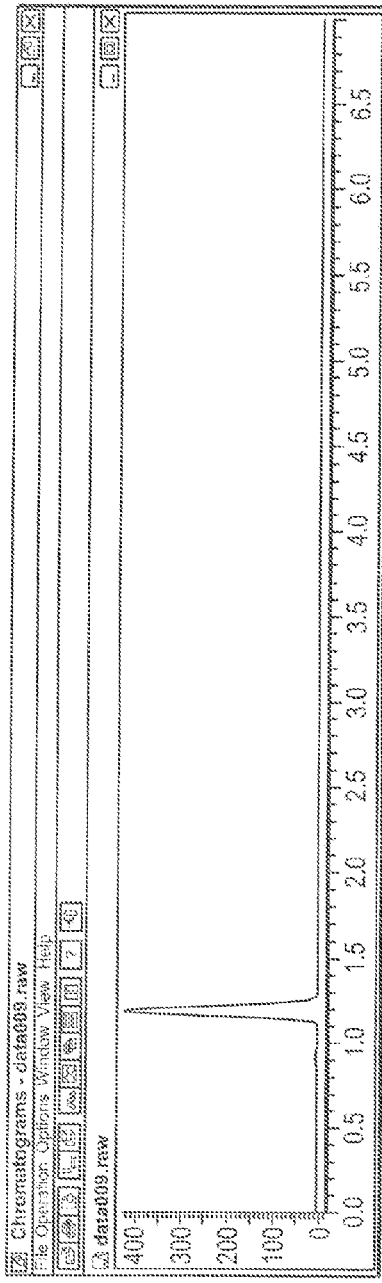
FIGS. 14A-14C are chromatograms of thiophene when tested using a Silconert-2000 coated jet assembly, in accordance with certain examples.
Figure 14B:
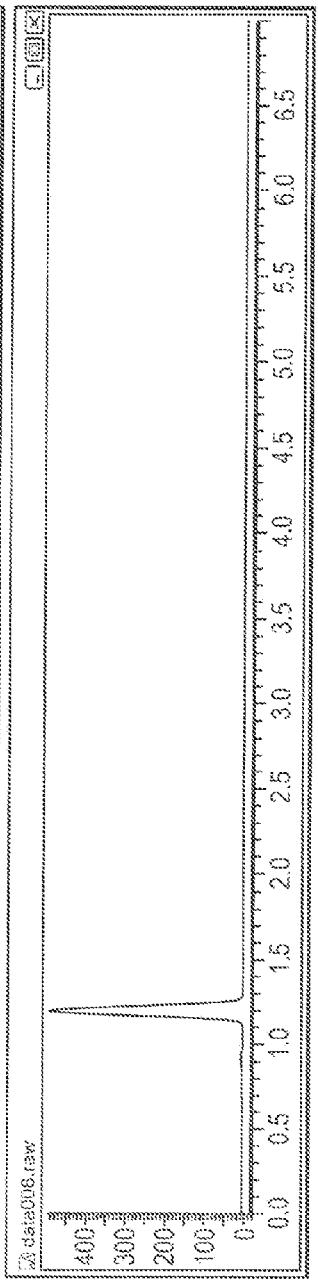
Figure 14C:
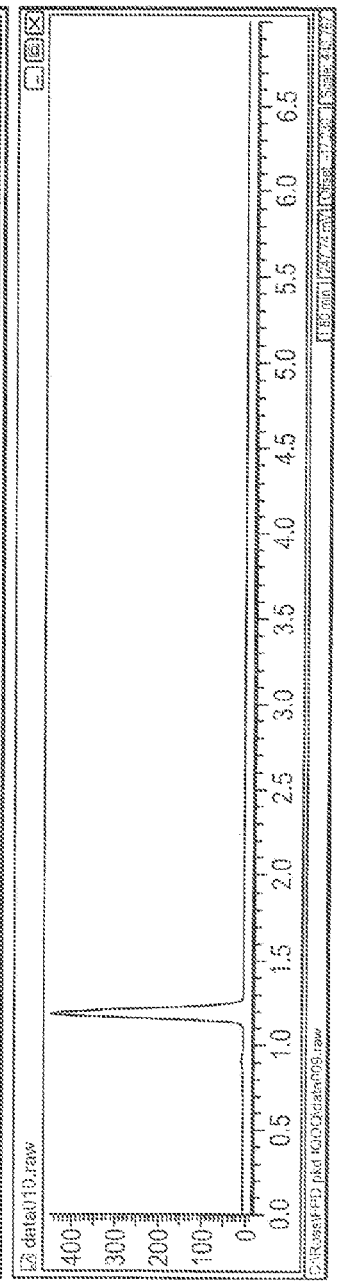
Figure 15A:
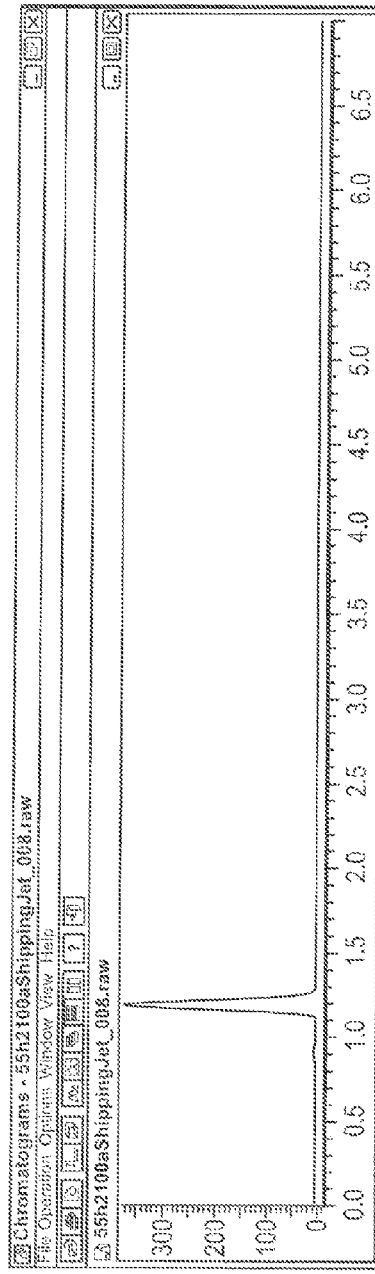
FIGS. 15A-15C are chromatograms of thiophene when tested using a non silica coated jet assembly, in accordance with certain examples.
Figure 15B:
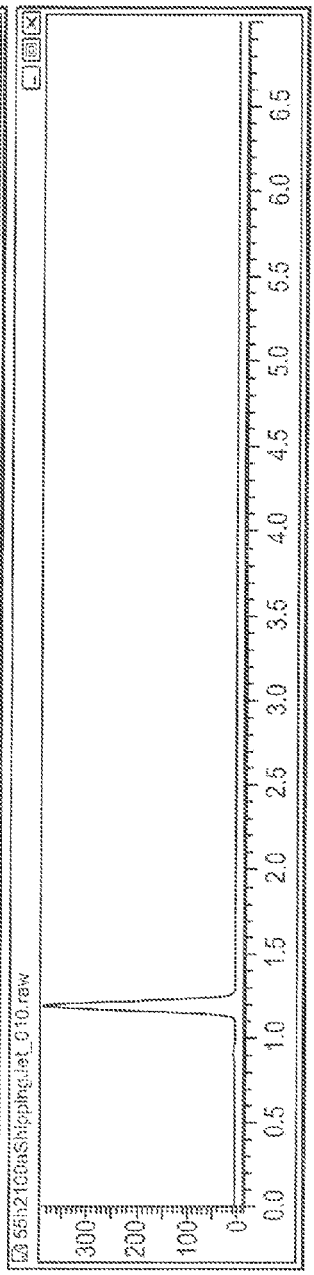
Figure 15C:
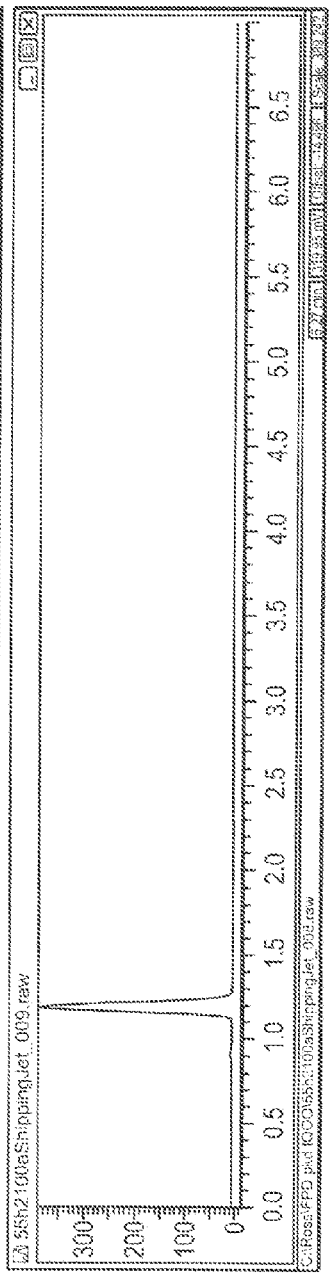

The jet assembly was tested using thiophene and the conditions listed in Examples 1 and 2. The results are shown in FIGS. 14A-14C (three separate runs). Chromatograms for an old jet are provided in FIGS. 15A-15C for comparison. The new FPD jet measured $5.25 \times 10^{-12}$ grams Sulfur/second which, is 1.9 times over the published minimum detectable quantity. The old jet, using the exact same method and standard, was $6.64 \times 10^{-12}$ grams sulfur/sec., which is 1.5 times the minimum detectable quantity. The retention times for the two jets were about the same, e.g., 1-2 minutes for thiophene. These results are consistent with the Silconert-2000 coated jet assembly providing suitable results for use with sulfur compounds.

Example 4

Figure 16A:
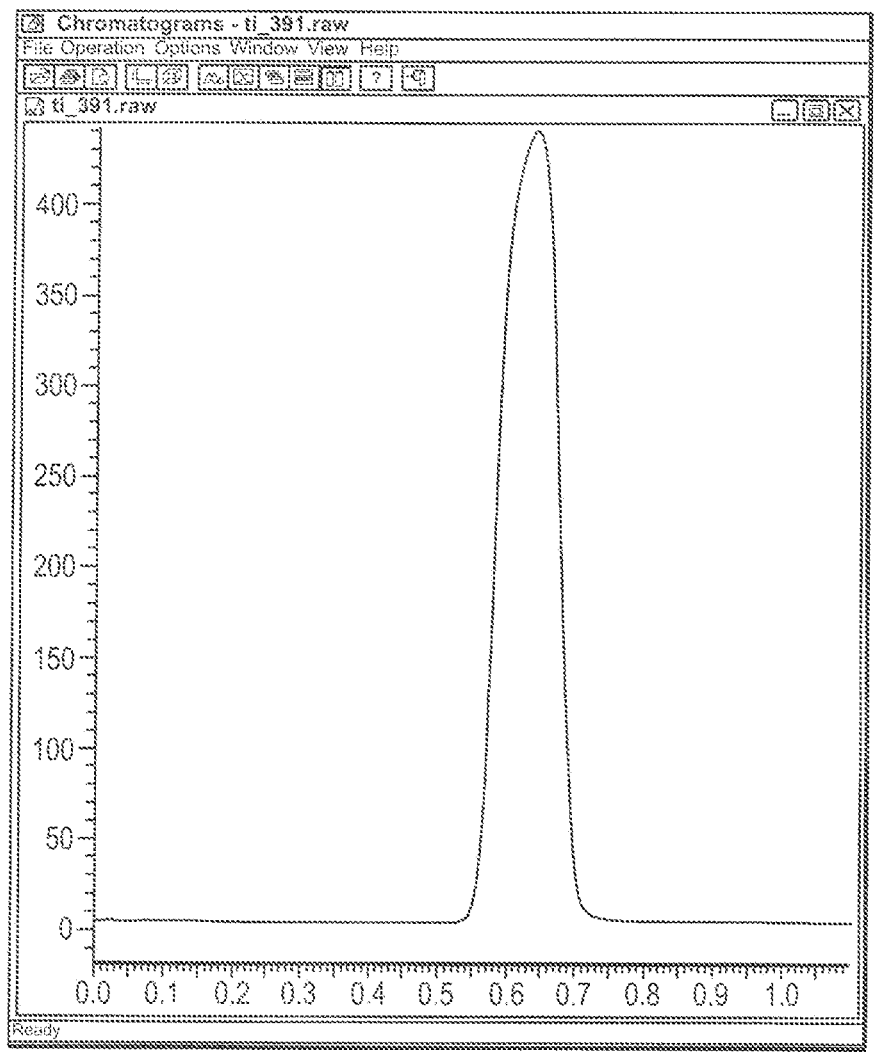
FIGS. 16A and 16B are chromatograms of $H_2S$ initial measurements using a Silconert-2000 coated jet assembly, in accordance with certain examples.
Figure 16B:
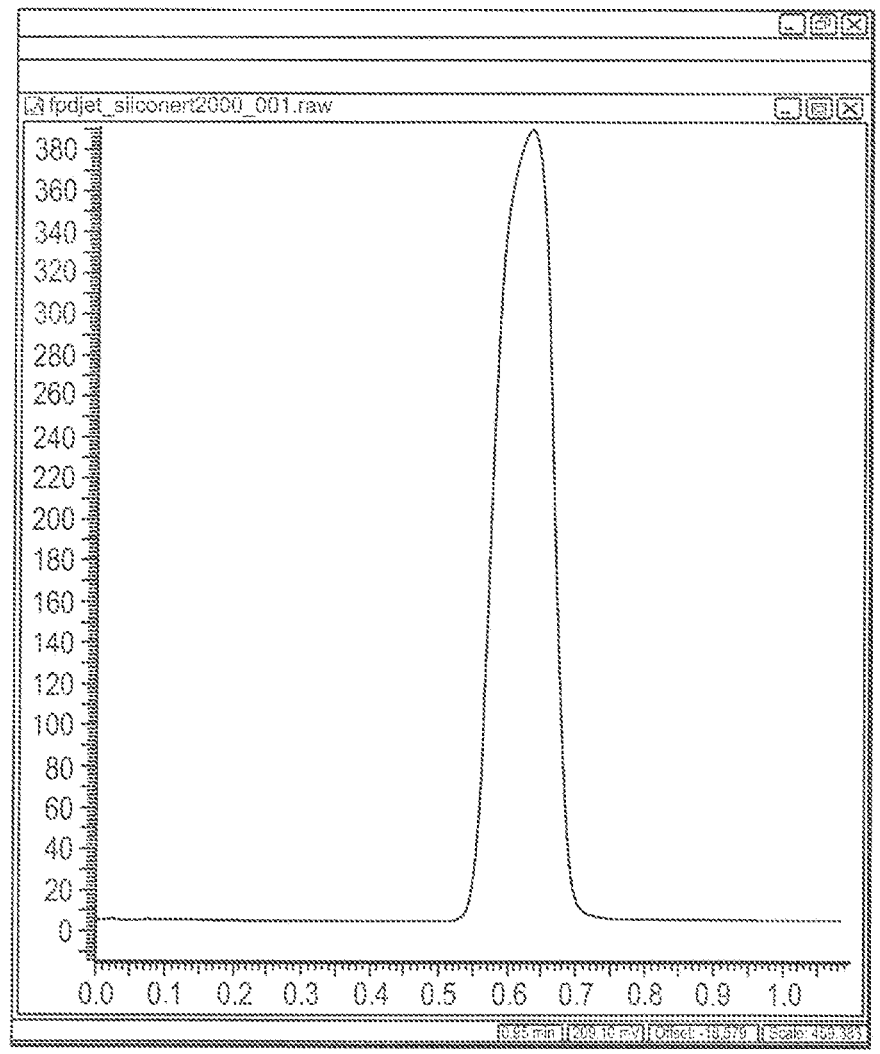
Figure 17A:
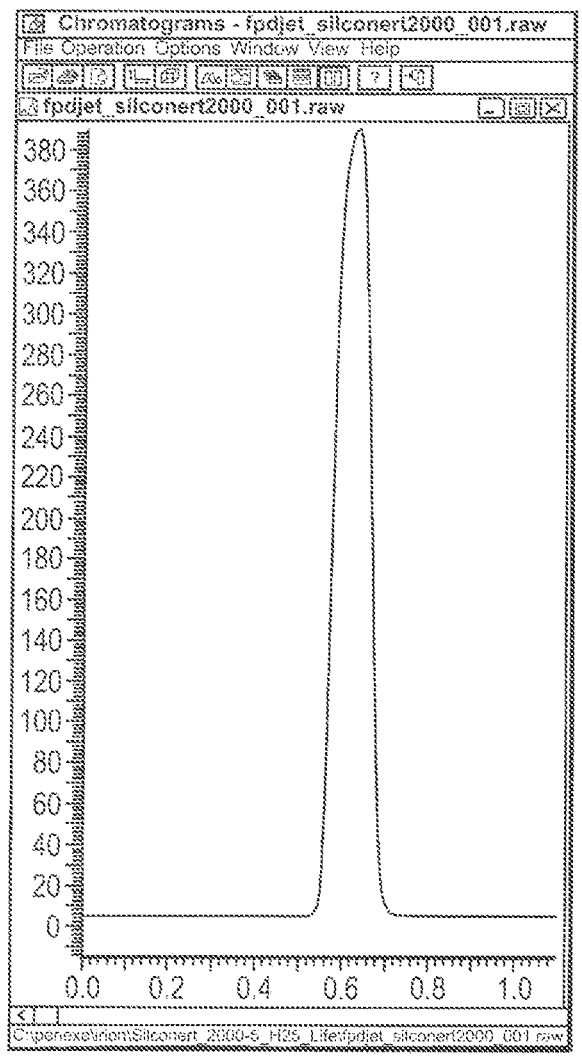
FIGS. 17A-17C are chromatograms of $H_2S$ measurements using the Silconet-2000 coated jet assembly, in accordance with certain examples.
Figure 17B:
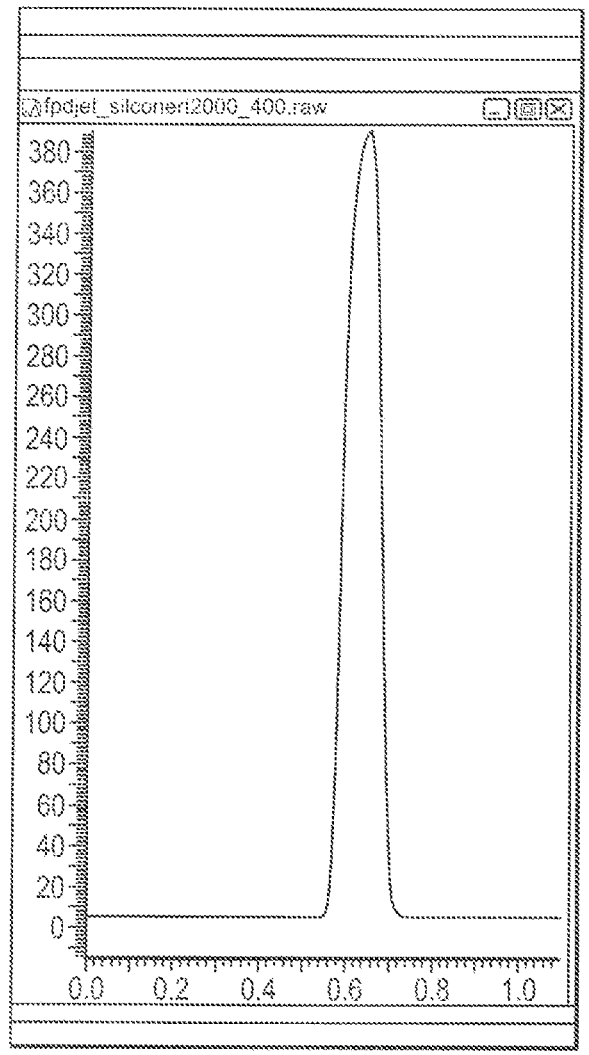
Figure 17C:
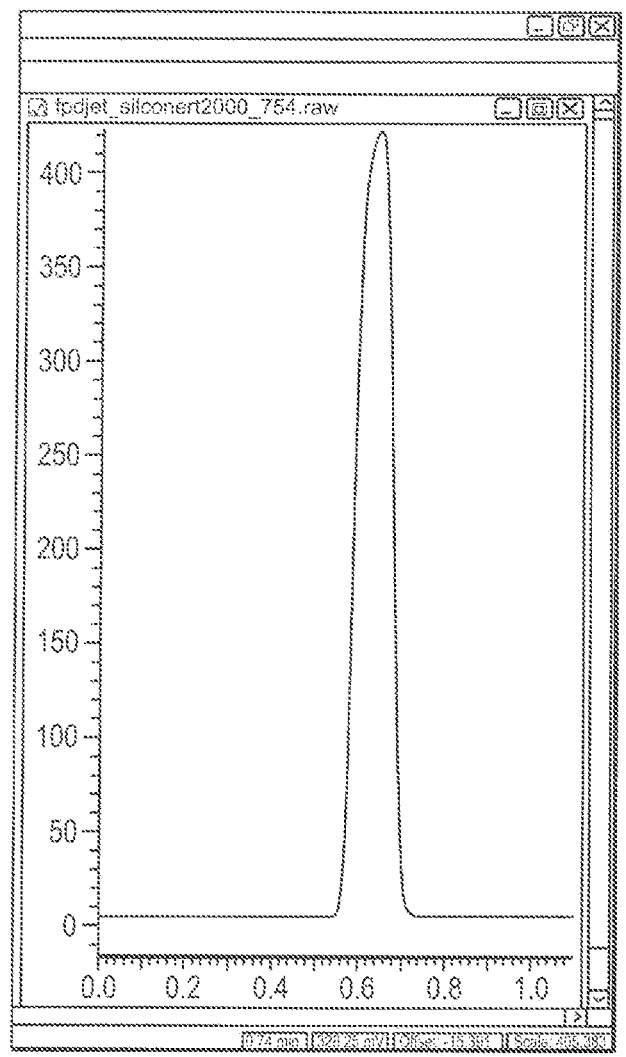
Figure 18A:
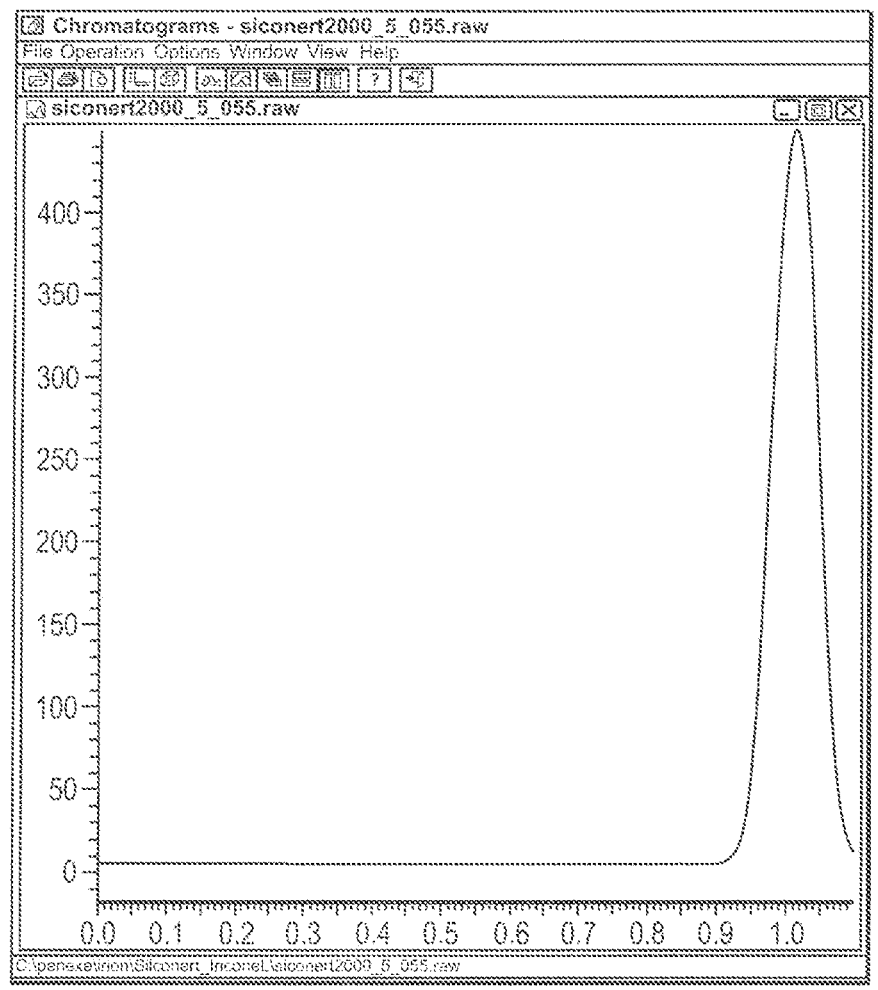
FIGS. 18A and 18B are chromatograms of $H_2S$ final measurements using a Silconert-2000 coated jet assembly, in accordance with certain examples.
Figure 18B:
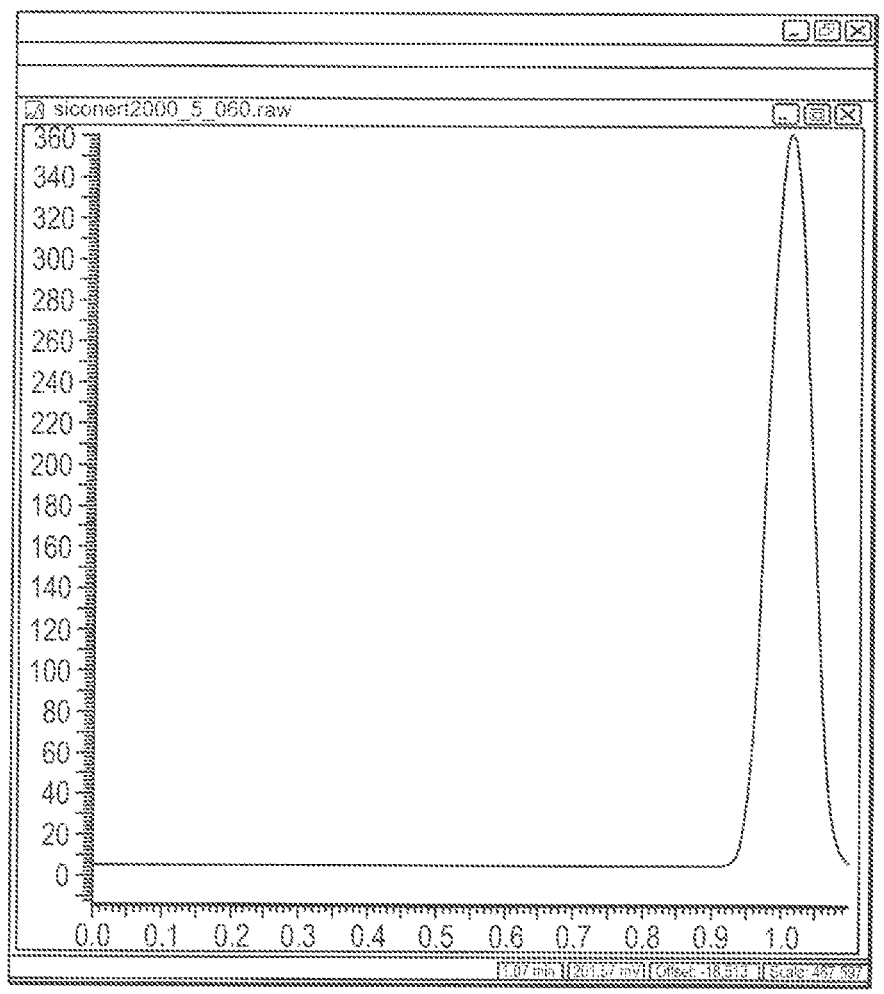

The jet assembly of Example 3 was tested using $H_2S$. FIGS. 16A and 16B are chromatograms showing the initial recovery of the jet at the initial injections using a control (fused silica tube and fused silica tube removed). 745 injections of $H_2S$ were then made. Illustrative chromatograms are shown in FIGS. 17A-17C. Measurements were then made with same the control (fused silica tube and fused silica tube removed) after the 745 injections to determine the recovery (see FIGS. 18A and 18B). Even after the 745 injections, the recovery of the coated jet assembly was substantially the same as the recovery upon initial injection. These results are consistent with the coated jet assembly providing a long usable life and minimal to no degradation during operation.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A jet assembly for use in a flame detector, the jet assembly comprising a flame jet configured to sustain a flame in the flame detector and a fluid flow path in a housing of the jet assembly, in which the fluid flow path is constructed and arranged to be fluidically coupled to a chromatography column at a column end to receive sample from the chromatography column, in which the fluid flow path is constructed and arranged to fluidically couple to the flame jet at a flame jet end, in which the entire fluid flow path from the column end to the flame jet end is formed from a substantially inert metal material, and in which the fluid flow path is present in the housing of the jet assembly without any brazes or welds.

2. The jet assembly of claim 1, in which the substantially inert metal material is present in an effective amount to deter catalysis in the fluid flow path.

3. The jet assembly of claim 1, in which the substantially inert metal material comprises titanium, aluminum, yttrium or combinations thereof.

4. The jet assembly of claim 3, in which the substantially inert metal material comprises titanium oxide, aluminum oxide, yttrium oxide or combinations thereof.

5. The jet assembly of claim 1, in which the substantially inert metal material comprises nickel.

6. The jet assembly of claim 5, in which the substantially inert metal material is a Hastelloy® alloy.

7. The jet assembly of claim 1, in which the substantially inert metal material comprises chromium.

8. The jet assembly of claim 7, in which the substantially inert metal material is an Inconel® alloy.

9. The jet assembly of claim 1, in which the substantially inert metal material is present in a tube that is integral to the housing.

10. The jet assembly of claim 1, in which the fluid flow path is provided by a tube assembly comprising an inner tube coupled to an outer tube, in which the inner tube is formed from the substantially inert metal material.

11. The jet assembly of claim 10, in which the inner tube is coupled to the outer tube without any brazes or welds.

12. A jet assembly for use in a flame detector, the jet assembly comprising a flame jet configured to sustain a flame in the flame detector and a fluid flow path in a housing of the jet assembly, in which the fluid flow path is constructed and arranged to be fluidically coupled to a chromatography column at a column end to receive sample from the chromatography column, in which the fluid flow path is constructed and arranged to fluidically couple to the flame jet at a flame jet end, in which the entire fluid flow path from the column end to the flame jet end is formed from a non-catalytic metal material present in an effective amount to deter catalysis in the fluid flow path, and in which the fluid flow path is present in the housing of the jet assembly without any brazes or welds.

13. The jet assembly of claim 12, in which the fluid flow path is a tube formed from the non-catalytic metal material.

14. The jet assembly of claim 12, in which the non-catalytic metal material comprises titanium, aluminum, yttrium or combinations thereof.

15. The jet assembly of claim 14, in which the non-catalytic metal material comprises titanium oxide, aluminum oxide, yttrium oxide or combinations thereof.

16. The jet assembly of claim 12, in which the non-catalytic metal material comprises nickel.

17. The jet assembly of claim 16, in which the non-catalytic metal material is a Hastelloy® alloy.

18. The jet assembly of claim 12, in which the non-catalytic metal material comprises chromium.

19. The jet assembly of claim 18, in which the non-catalytic metal material is an Inconel® alloy.

20. The jet assembly of claim 12, in which the fluid flow path is provided by a tube assembly comprising an inner tube couple to an outer tube, in which the inner tube is formed from the non-catalytic metal material present in an effective amount to deter catalysis in the fluid flow path.

21. The jet assembly of claim 20, in which the inner tube is coupled to the outer tube without any brazes or welds.

* * * * *